US008846073B2

(12) United States Patent
Spada et al.

(10) Patent No.: US 8,846,073 B2
(45) Date of Patent: Sep. 30, 2014

(54) LOW TEMPERATURE PROCESSES FOR MAKING CYCLIC LIPID IMPLANTS FOR INTRAOCULAR USE

(75) Inventors: Lon T. Spada, Walnut, CA (US); James N. Chang, Newport Beach, CA (US); Michelle Luu, Anaheim, CA (US)

(73) Assignee: Allergan, Inc., Irvine, CA (US)

( * ) Notice: Subject to any disclaimer, the term of this patent is extended or adjusted under 35 U.S.C. 154(b) by 1489 days.

(21) Appl. No.: 11/612,928

(22) Filed: Dec. 19, 2006

(65) Prior Publication Data

US 2008/0145403 A1 Jun. 19, 2008

(51) Int. Cl.
A61F 2/00 (2006.01)
A61K 31/165 (2006.01)
A61K 9/00 (2006.01)
A61K 31/557 (2006.01)
A61K 9/14 (2006.01)

(52) U.S. Cl.
CPC ............... *A61K 31/165* (2013.01); *A61K 9/141* (2013.01); *A61K 9/0051* (2013.01); *A61K 31/557* (2013.01)
USPC ........................................................ 424/428

(58) Field of Classification Search
USPC ........................................................ 424/428
See application file for complete search history.

(56) References Cited

U.S. PATENT DOCUMENTS

| | | | |
|---|---|---|---|
| 4,327,725 A | 5/1982 | Cortese | |
| 4,474,451 A | 10/1984 | Mizokami | |
| 4,521,210 A | 6/1985 | Wong | |
| 4,853,224 A | 8/1989 | Wong | |
| 4,997,652 A | 3/1991 | Wong | |
| 5,164,188 A | 11/1992 | Wong | |
| 5,443,505 A | 8/1995 | Wong | |
| 5,501,856 A | 3/1996 | Ohtori | |
| 5,766,242 A | 6/1998 | Wong | |
| 5,824,072 A | 10/1998 | Wong | |
| 5,869,079 A | 2/1999 | Wong | |
| 5,882,327 A * | 3/1999 | Jacob | 604/8 |
| 6,074,661 A | 6/2000 | Olejnik | |
| 6,309,669 B1 | 10/2001 | Setterstrom et al. | |
| 6,331,313 B1 | 12/2001 | Wong | |
| 6,369,116 B1 | 4/2002 | Wong | |
| 6,699,493 B2 | 3/2004 | Wong | |
| 2002/0009493 A1 | 1/2002 | Schwendeman et al. | |
| 2002/0035264 A1 | 3/2002 | Kararli | |
| 2003/0069560 A1 | 4/2003 | Adamis et al. | |
| 2004/0151753 A1 | 8/2004 | Chen et al. | |
| 2004/0175410 A1 | 9/2004 | Ashton | |
| 2005/0048099 A1 | 3/2005 | Shiah | |
| 2005/0244464 A1 * | 11/2005 | Hughes | 424/427 |
| 2006/0210604 A1 | 9/2006 | Dadey | |
| 2006/0233860 A1 | 10/2006 | Chang et al. | |
| 2007/0212395 A1 | 9/2007 | Donello et al. | |
| 2008/0033351 A1 | 2/2008 | Trogden et al. | |
| 2008/0107694 A1 | 5/2008 | Trogden et al. | |
| 2008/0131484 A1 | 6/2008 | Robinson | |
| 2008/0292679 A1 | 11/2008 | Lyons et al. | |
| 2010/0278898 A1 | 11/2010 | Hughes et al. | |

FOREIGN PATENT DOCUMENTS

| | | |
|---|---|---|
| EP | 0251476 | 1/1988 |
| EP | 1842507 | 10/2007 |
| WO | 94-14417 | 7/1994 |
| WO | 00-37056 | 6/2000 |
| WO | WO2006/031658 A | 3/2006 |
| WO | WO 2006031658 A2 * | 3/2006 |
| WO | 2006-041942 A2 | 4/2006 |
| WO | 2008-070402 A2 | 6/2008 |

OTHER PUBLICATIONS

MerckSource, Dorland's Medical Dictionary-Analgoue, 2007, printed Feb. 17, 2009 from http://www.mercksource.com/pp/us/cns/cns_hl_dorlands_split.jsp?pg=/ppdocs/us/common/dorlands/dorland/one/000004228.htm, 2 pages.*
Gujarat Chemicals, Polyethylene Glycol, Aug. 14, 2004, Google date sheet included, printed from http://www.gujchem.com/polyethylene-gycol.html, 5 pages.*
Merkli A et al: "Use of insoluble Biodegradable Polymers in Ophthalmic Systems for the Sustained Release of Drugs" European Journal of Pharmaceutics and Biopharmaceutics, Elsevier Science Publishers B.V., Amsterdam, NL, vol. 41, No. 5, Oct. 1, 1995, pp. 271-283.
Cantor, L., *Bimatoprost: a member of a new class of agents, the prostamides for glaucoma management*, Exp Opin Invest Drugs (2001); 10(4): 721-731.
Forster, A., et al., *Selection of excipients for melt extrusion with two poorly water-soluble drugs by solubility parameter calculation and thermal analysis*, Int J Pharmaceutics 226 (2001) 147-161.
U.S. Appl. No. 10/837,260, filed Apr. 30, 2004, Hughes.
U.S. Appl. No. 11/368,845, filed Mar. 6, 2006, Hughes.
Ladewig M.S. et al., Prostaglandins Leukot. Essent. Fatty Acids 72:251-6 (Apr. 2005).
Siemann U., *Densitometric determination of the solubility parameters of biodegradable polyesters*, Proceed Intern Symp Control Rel Bioact Mater 12 (1985):53-54.
Woodward D., et al., *The Pharmacology of Bimatoprost (Lumigan™ )*, Surv Ophthalmol May 2001; 45 (Suppl 4): S337-S345.
International Search Report dated Feb. 25, 2009, PCT/US2007/087139.
U.S. Appl. No. 11/565,917, filed Dec. 1, 2006.

* cited by examiner

*Primary Examiner* — Gigi Huang
(74) *Attorney, Agent, or Firm* — Jennifer C. Cheng

(57) ABSTRACT

Biocompatible implants comprising a cyclic lipid therapeutic agent are made using a low temperature melt extrusion process. The implants are suitable for intraocular use to treat an ocular condition.

5 Claims, 2 Drawing Sheets

Figure 1. Effect of Temperature on Bimatoprost Potency
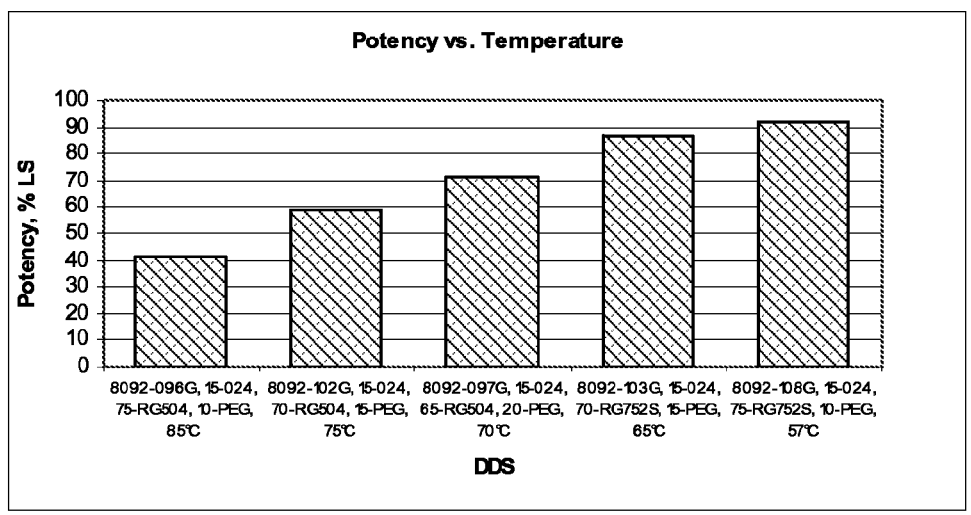
Figure 2. Total Percent Release of Bimatoprost in pH 7.4 PBS at 37°C
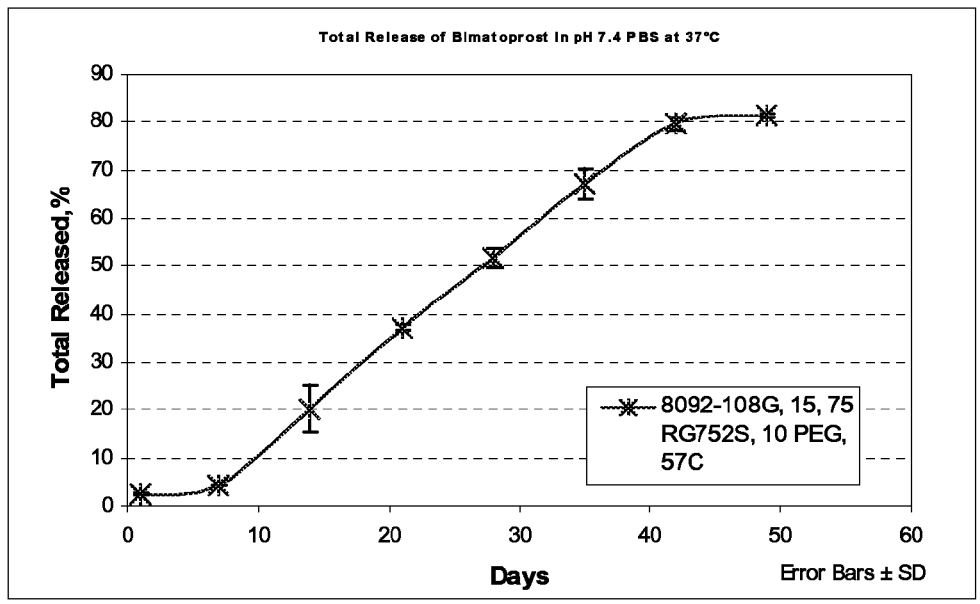

Figure 3. Daily Release Rate of Bimatoprost Over 50 Day Period
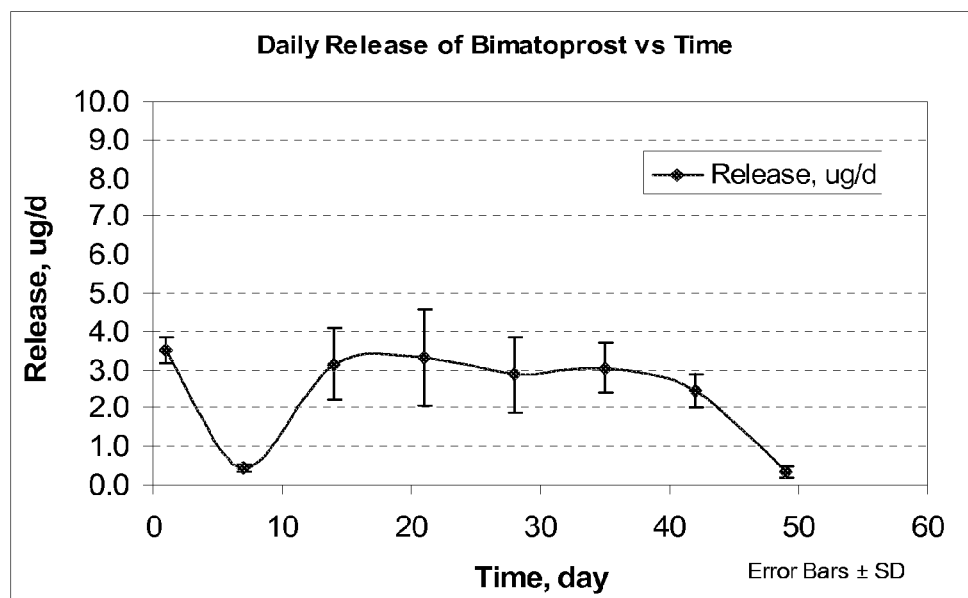

LOW TEMPERATURE PROCESSES FOR MAKING CYCLIC LIPID IMPLANTS FOR INTRAOCULAR USE

BACKGROUND

The present invention relates to processes for making an intraocular implant and the implants thereby made. In particular, the present invention relates to low temperature processes for making implants suitable for intraocular use.

It is known to make drug delivery systems suitable for intraocular use ("implants"). An implant can comprise one or more therapeutic agents as well as one or more biodegradable or non-biodegradable carriers (such as a polymeric or non-polymeric carrier). Typically, the carrier comprises the bulk (i.e. more than 50%) of the implant by weight and can function to hold (the carrier function) and then release the therapeutic agent in vivo, for example as a biodegradable or bio-erodible carrier is degraded in situ at or in proximity to the ocular tissue target site. Biocompatible implants for placement in the eye have been disclosed in a number of patents, such as U.S. Pat. Nos. 4,521,210; 4,853,224; 4,997,652; 5,164,188; 5,443,505; 5,501,856; 5,766,242; 5,824,072; 5,869,079; 6,074,661; 6,331,313; 6,369,116; and 6,699,493.

Implants suitable for intraocular use have been made by various methods including compression, solvent evaporation and extrusion methods. An extrusion method for making an intraocular implant can be carried out by first mixing a therapeutic agent with a polymer or polymers. Typically, solid forms (i.e. powders) of the therapeutic agent and the polymers are mixed together to achieve a homogenous mixture of the powders. As noted, the polymer can function as a carrier for the therapeutic agent. Thus, if a biodegradable polymer is used the therapeutic agent can diffuse out of the polymer upon intraocular insertion or implantation of the implant, as the polymer degrades. Although the therapeutic agent-polymer mixture can be compressed to form a tablet, an extruded implant can exhibit a more desirable release profile for the therapeutic agent. Hence, an implant with superior characteristics can be made by heating the therapeutic agent-polymer mixture to the temperature at which the polymer melts, followed by extrusion of an implant with desired dimensions. Melting the polymer helps ensure an even distribution of the active agent within the polymeric matrix and upon cooling provides a solid form implant. It is known to make extruded implants for intraocular use in which the therapeutic agent-polymer mixture is heated to about 90° C. to about 115° C. prior to being extruded. See eg published U.S. patent application number 20050 048099.

Unfortunately heating the therapeutic agent-polymer mixture to a temperature at which the polymer melts can have undesirable or destabilization effects. For example, heating the polymer to its melt temperature can result in the formation of degradation products and/or aggregates of either or both the therapeutic agent and the polymer. This can result in the materials potentially toxic or immunogenic to sensitive ocular tissues and/or can interfere with obtaining a desired release profile of the therapeutic agent from the extruded implant. Additionally, heating the therapeutic agent to the melt temperature of the polymeric carrier (so as to provide a homogenous dispersion of the therapeutic agent in the polymeric matrix) can reduce the potency of a heat sensitive therapeutic agent, thereby reducing the therapeutic efficacy of the resulting implant.

Another problem with existing implants can arise from the presence of polymorphs of the therapeutic agent. A polymorph is a substance which has a chemical composition identical to that of another substance but which exists in a different crystal structure (eg diamond and graphite). Different polymorphs of a substance can have different stabilities, solubilities and, for a therapeutic agent, different potencies or therapeutic efficacies. With known implants, a crystalline therapeutic agent is typically melted along with its polymeric matrix and may recrystallize upon formation of the solid implant. Alternately, the crystalline therapeutic agent can be mixed with the polymer without melting the therapeutic agent. In either case, the therapeutic agent is present in the final implant as crystals (i.e. as particles) of the therapeutic agent dispersed throughout the polymeric matrix. Hence, with either known method for making an implant the therapeutic agent is present in polymorphic forms, each of which therapeutic agent polymorph can have a different therapeutic efficacy.

Hypotensive therapeutic agents are useful in the treatment of a number of various ocular hypertensive conditions, such as post-surgical and post-laser trabeculectomy ocular hypertensive episodes, glaucoma, and as presurgical adjuncts. Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The increased intraocular pressure characteristic of glaucoma can be due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupillary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical beta-adrenoreceptor antagonists have traditionally been the drugs of choice for treating glaucoma.

Some prostaglandins are utility as ocular hypotensive agents, including $PGF_{2\alpha}$, $PGF_{1\alpha}$, $PGE_2$, and certain lipid-soluble esters, such as $C_1$ to $C_5$ alkyl esters, e.g. 1-isopropyl ester, of such compounds. Unfortunately, ocular surface (conjunctival) hyperemia and foreign-body sensation have been consistently associated with topical ocular use of prostaglandins as anti-hypertensive agent (i.e. to treat glaucoma), including $PGF_{2\alpha}$ and its prodrugs, e.g. its 1-isopropyl ester. The $PGF_{2\alpha}$ derivative latanoprost is sold under the trademark Xalatan® for treating ocular hypertension and glaucoma. Topical use of latanoprost can have the undesirable side effect of turning the iris of a user brown.

In Laedwif M. S. et al., PROSTAGLANDINS LEUKOT. ESSENT. FATTY ACIDS 72:251-6 (April 2005), it was disclosed that infusion of with a cyclic lipid (prostaglandin E1) in patients with age-related macular degeneration (ARMD) resulted in an improvement in visual acuity.

Bimatoprost is an analog (that is a structural derivative) of a naturally occurring prostamide. The formula for bimatoprost ($C_{25}H_{37}NO_4$) is ((Z)-7-[1R,2R,3R,5S)-3,5-Dihydoxy-2-[1E,3S)-3-hydroxy-5-phenyl-1-pentenyl]cyclopentyl]-5-N-ethylheptenamide. Its' molecular weight is 415.58. Bimatoprost is a heat sensitive molecule, meaning that it can degrade if heated to a temperature greater than about 65° C. In a low pH environment bimatoprost can degrade at a lower temperature and at a faster rate. Bimatoprost has several polymorphic crystal structures. Not all the polymorphs of bimatoprost have the same level of biological activity. Bimatoprost is slightly soluble in water (by definition 3 mg of a water soluble substance can be dissolved in one mL of water at 25° C.).

Bimatoprost can be used to reduce intraocular pressure. See eg Cantor, L., *Bimatoprost: a member of a new class of agents, the prostamides for glaucoma management*, Exp Opin Invest Drugs (2001); 10(4): 721-731, and; Woodward D., et al., *The Pharmacology of Bimatoprost* (Lumigan™), Surv Ophthalmol 2001 May; 45 (Suppl 4): S337-S345. An ophthalmic solution of 0.03% bimatoprost is sold by Allergan (Irvine, Calif.) under the trademark Lumigan®. Lumigan® is an effective treatment for ocular hypotension and glaucoma and is administered topically to the effected eye topically once a day. Each mL of Lumigan® contains 0.3 mg of bimatoprost as the active agent, 0.05 mg of benzalkonium chloride (BAK) as a preservative, and sodium chloride, sodium phosphate, dibasic; citric acid; and purified water as inactive agents.

It is known to make bimatoprost containing implants for intraocular use. See eg U.S. patents application Ser. Nos. 10/837,260 and 11/368,845.

Polymer Solubility Parameters

A solubility parameter for a substance is a numerical value which indicates the relative solvency behavior of that substance. The solubility parameter is derived from the cohesive energy density of the substance, which in turn is derived from the heat of vaporization. The heat of vaporization of a substance is the energy required to vaporize (render into a gas) the substance. From the heat of vaporization (in calories per cubic centimeter of a liquid substance), one can derive the cohesive energy density (c):

$$c = \frac{\Delta H - RT}{V_m} \quad (1)$$

where: c=cohesive energy density; ΔHv=heat of vaporization; R=a gas constant; T=Temperature, and $V_m$=molar volume. The cohesive energy density (c) of a liquid is a numerical value that indicates the energy of vaporization in calories per cubic centimeter, and is a direct reflection of the degree of van der Waals forces holding the molecules of the liquid together. Since the solubility of two materials is only possible when their intermolecular attractive forces are similar, materials with similar cohesive energy density values are miscible in each other.

The square root of the cohesive energy density (c) provides a solubility parameter for a substance:

$$\partial = \sqrt{c} = \left[\frac{\Delta H - RT}{V_m}\right]^{1/2} \quad (2)$$

This solubility parameter can be represented as delta (δ). δ can be expressed in calories/cc (the standard or older parameter) or in standard international units (SI units). The SI unit is in pascals. Thus, one MPa is one milliPascal. SI parameters are about twice the value of the standard solubility parameter units:

$$\delta/cal^{1/2} \, cm^{-3/2} = 0.48888 \times \delta/MPa^{1/2} \quad (3)$$

$$\delta/MPa^{1/2} = 2.0455 \times \delta/cal^{1/2} cm^{-3/2} \quad (4)$$

The newer SI units for the solubility parameter of a substance are usually designated as $\delta/MPa^{1/2}$ (sometimes shown in a shorthand version as just $MPa^{1/2}$) or δ(SI).

Since a polymer will typically decompose before its heat of vaporization could be measured, swelling behavior is one of the ways that a solubility parameter can be determined for a polymer. The term cohesion parameter can be used to mean the solubility parameter of a non-liquid material. The solubility parameters for biodegradable polymers can be determined. See e.g. Siemann U., *Densitometric determination of the solubility parameters of biodegradable polyesters*, Proceed Intern Symp Control Rel Bioact Mater 12 (1985):53-54. As noted above, $MPa^{1/2}$ is a standard unit for solubility parameter. The solubility parameter δ is equal to $c^{1/2}$, where $c=(\Delta E/V_m)^{1/2}$. In short two materials will mix if their ΔG<0, and ΔG=ΔH−TΔS (this is the formula for Gibbs Free Energy [ΔG] which defines the free energy of a reaction, where ΔH is the change in enthalpy in a constant pressure process and ΔS is the change in entropy). ΔS is always positive for mixing, but ΔH depends roughly on $\Delta H \sim Vm\phi_1\phi_2(\delta_1-\delta_2)^{1/2}$ where "1" and "2" are the two components. The closer the δ's are to each other, the closer ΔH is to zero and the more energetically favorable the combination.

A solid solution is a solid state solution of one or more solutes in a solvent. A solute initially in a crystalline form which enters into solid solution is no longer in a crystalline form, as is it in a solution, albeit in this case in a solid state solution. Some mixtures will readily form solid solutions over a range of concentrations, while other mixtures will not form solid solutions at all. The propensity for any two substances to form a solid solution is a complicated matter involving the chemical, crystallographic, and quantum properties of the substances in question. For example, solid solutions can form if the solute and solvent have similar atomic radii (15% or less difference), same crystal structure, similar electronegativities and/or similar valance. It is known to compare the solubility parameters of a water soluble drug and a single polymeric excipient to determine if they are miscible in each other so that a glass solution will be formed upon melt extrusion. Forster, A., et al., *Selection of excipients for melt extrusion with two poorly water-soluble drugs by solubility parameter calculation and thermal analysis*, Int J Pharmaceutics 226 (2001) 147-161. The ability of one solid to function as a cosolvent (i.e. to solubilize) of another solid (i.e. a polymer) upon formation of a solid solution of the two solids can depend upon the ability of the cosolvent to function as a plasticizer of the polymer and/or due to the relative similarities of their solubility parameters.

Polyethylene Glycol

Polyethylene glycol ("PEG") has the general formula $C_{2n}H_{4n+2}O_{n+1}$, which can be represented as:

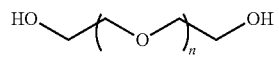

Being a polymer, a polyethylene glycol has a glass transition temperature ($T_g$) (which can be the same as or different from the softening point or the melt temperature of the polymer), as opposed to a true melting point. Within in a certain range the glass transition temperature of a polyethylene glycol increases as its molecular weight increases. For example PEG 400 has a $T_g$ of 4-8° C., PEG 600 has a $T_g$ of 20-25° C., PEG 1500 has a $T_g$ of 44-48° C., PEG 4000 has a $T_g$ of 54-58° C., and PEG 6000 has a $T_g$ of 56-63° C. Poly(ethylene glycol) is non-toxic, water soluble polymer used in a variety of products. For example it is used in laxatives, skin creams and toothpastes.

PEG-3350 [HO($C_2H_4O$)$_n$] is a synthetic polyglycol having an average molecular weight of 3350.

What is needed therefore is a process for making an intraocular implant from a therapeutic agent and a polymer which does not result in or which reduces the occurrence of undesirable therapeutic agent and/or polymer end products or crystalline forms of the therapeutic agent in the implant.

SUMMARY

The present invention meets this need and provides a process for making an intraocular implant comprising a therapeutic agent and a polymer which process does not result in or which reduces the occurrence of undesirable therapeutic agent and/or polymer end products in the implant. Additionally, the therapeutic agent is not present in the implant in a crystalline form, so no polymorphs of the therapeutic agent are present in the implant. The present invention can meet this need by providing a low temperature melt extrusion method for making an implant suitable for intraocular use, the implant comprising a therapeutic agent and a suitable polymer.

The present processes provide extended and sustained release implants comprising one or more ophthalmically active cyclic lipid therapeutic agents. Thus, the patient in whose eye the implant have been placed receives a therapeutic amount of a cyclic lipid therapeutic agent for a relatively long or extended time period without requiring additional administrations of the agent or agents. The patient thereby has a therapeutically active agent available for treatment of the eye over a relatively long period of time, for example, on the order of at least about one week, such as between about two and about six months after administering the implant. Such extended release times facilitate obtaining successful treatment of ocular conditions. In addition, administering such implants preferably subconjunctivally can reduce the occurrence and/or severity of at least one side effect, for example, hyperemia, relative to administering an identical amount of the cyclic lipid therapeutic agent to the eye in the form of a topical composition. Further, subconjunctival administration of an implant comprising a cyclic lipid therapeutic agent can be effective to provide a cyclic lipid therapeutic agent to the retina to treat a retinal disease or condition. As the subconjunctival administration of an implant containing a cyclic lipid therapeutic agent results in particularly effective delivery of such agents to the retina, the present invention provides a particularly advantageous method of delivering a cyclic lipid therapeutic agent to ocular tissues without the side effects which can result from systemic administration.

Implants in accordance with our invention comprise a cyclic lipid therapeutic agent and a drug release sustaining component (such as a suitable polymer) associated with the cyclic lipid therapeutic agent. In accordance with the present invention, the cyclic lipid therapeutic agent can comprise, consists essentially of, or consists of a prostaglandin, prostaglandin analog, prostaglandin derivative, prostamide, prostamide analog, and a prostamide derivative that is effective in treating an ocular condition, such as for example reducing or maintaining a reduced intraocular pressure in a hypertensive eye, or providing to the retina of an eye an effective amount of a cyclic lipid therapeutic agent having neuroprotective activities. The polymer is associated with the cyclic lipid therapeutic agent to sustain release of an amount of the cyclic lipid therapeutic agent into an eye in which the implant is placed. The cyclic lipid therapeutic agent is released into the eye for an extended period of time after the implant is are administered, for example, subconjunctivally and is effective in treating or reducing at least one symptom of an ocular condition. The present implants can relieve ocular hypertension by reducing the intraocular pressure of the eye or maintaining the intraocular pressure at a reduced level without substantial amounts of ocular hyperemia. Alternatively, the present implants can relieve disorders of the posterior segment of the eye, particularly, a retinal condition such as exudative or non-exudative age-related macular degeneration, by delivering a cyclic lipid therapeutic agent via the sclera to the tissues of the posterior segment, in particular, the retina.

In one embodiment the implants comprise a cyclic lipid therapeutic agent and a biodegradable polymer matrix. The cyclic lipid therapeutic agent is associated with a biodegradable polymer matrix that releases drug at a rate effective to sustain release of an amount of the cyclic lipid therapeutic agent from the implant effective to treat an ocular condition. The implants can be biodegradable or bioerodible and provide a sustained release of the cyclic lipid therapeutic agent to either or both the anterior and posterior segments of the eye for extended periods of time, such as for more than one week, for example for about three months or more and up to about six months or more.

The biodegradable polymer component of the implants can be a mixture of biodegradable polymers having a molecular weight between about 1000 kiloDaltons (kD) and about 10 kD. For example, the biodegradable polymer can comprise a polylactic acid polymer having a molecular weight between about 500 kD and about 50 kD, and preferably less than about 64 kiloDaltons. Additionally or alternatively, the implants can comprise a first biodegradable polymer of a polylactic acid, and a different second biodegradable polymer of a polylactic acid. Furthermore, the implants can comprise a mixture of different biodegradable polymers, each biodegradable polymer having an inherent viscosity in a range of about 0.2 deciliters/gram (dL/g) to about 1.0 dL/g.

The cyclic lipid therapeutic agent of the implants disclosed herein can include a prostaglandin, prostaglandin analog, prostaglandin derivative, prostamide, prostamide analog, or a prostamide derivative, that is effective in treating ocular conditions. One example of a suitable prostamide derivative is bimatoprost. An embodiment of our invention is a sustained release bimatoprost implant, preferably implanted in the subconjunctiva of the eye, to thereby remove the need for daily administration of the bimatoprost. The sustained release implant can provide a controlled release of this hypotensive agent over an extended period of time.

Other examples of cyclic lipid therapeutic agent within the scope of our invention include, without limitation, latanoprost, travoprost and unoprostone and salts derivatives, and analogs of these. In addition, the implant can be formulated with cyclic lipid therapeutic as well as one or more additional and different therapeutic agents that can be effective to treat an ocular condition.

A process for making the present implants involves combining or mixing the cyclic lipid therapeutic agent with a biodegradable polymer or polymers. The mixture can then be extruded, compressed or solvent cast to form a single composition. The single composition can then be processed to form an implant suitable for placement at an ocular location, such as for example at a subconjunctival, sub tenon, intravitreal or intrascleral location.

The implant can be placed in an ocular region such as, without limitation, subconjunctivally, to treat a variety of ocular conditions of the anterior or posterior segment. For example, the implant can deliver a cyclic lipid therapeutic agent to tissues of the anterior segment, thereby reducing ocular hypertension, and thus may be effective in reducing at least one symptom of an ocular condition associated with an increased intraocular pressure. Alternatively, subconjunctival administration of the implant of the present invention can be effective to deliver the cyclic lipid therapeutic agent to the retina and other tissues of the posterior segment for the treatment of neurodegenerative conditions such as age related macular degeneration (ARMD), such as "wet" or "dry" ARMD.

Our invention also encompasses the use of a cyclic lipid therapeutic agent and a polymeric component, as described herein, in the manufacture of a medicament for treating a patient.

Low Temperature Extrusion Processes

Our invention encompasses a low temperature process for making an intraocular implant. The process is carried out by combining a cyclic lipid therapeutic agent and a polymer to form a mixture. The mixture is then heated to a temperature between about 50° C. and about 80° C., followed by extruding the heated mixture to thereby make an implant suitable for intraocular use. By "low temperature" process is it meant a process which is carried out at a temperature between about 50° C. and about 80° C. The implant made by this process is an intraocular implant, meaning that the implant is structured and configured so as to be suitable for insertion or implantation within an ocular tissue or within an ocular space or virtual ocular space. Thus, an implant made by our process is suitable for insertion or implantation into, for example, the anterior chamber, the posterior chamber, the vitreous cavity, the choroid, the suprachoroidal space, the subretinal space, the conjunctiva, the subconjunctival space, the episcleral space, the intracorneal space, the epicorneal space, the sclera, the pars plana, surgically-induced avascular regions, the macula, the retina and sub-tenon locations. Preferably, when the implant contains an antihypertensive therapeutic agent (such as a prostaglandin analog, an alpha adrenergic receptor agonist or a beta blocker) the implant is implanted or inserted subconjunctivally so as to be placed at a location proximate to the cilliary body, a target tissue for an antihypertensive therapeutic agent.

Because our low temperature process results in an implant suitable or intraocular use, therefore topical (i.e. as eye drops) and systemic route of administrations are outside the scope of our invention. Additionally, the implants made by a process within the scope of our invention are not microparticles or microspheres (a microparticle or microsphere has a diameter of from about 0.1μ to about 5 microns) in diameter but are instead discrete solid body implants (from about 0.1 mm up to about 10 mm in diameter) intended for intraocular administration as single, or as a small number (i.e. five or less) implants, as opposed to administration of a population of hundreds or thousands of microparticles or microspheres.

In a low temperature process for making an intraocular implant with the scope of our invention the cyclic lipid therapeutic agent can be a prostaglandin, a prostaglandin analog, or and mixture thereof. For example, the cyclic lipid therapeutic agent can be bimatoprost, a bimatoprost analog, latanoprost, a latanoprost analog, travoprost, a travoprost analog, unoprostone, a unoprostone analog, prostaglandin E1, a prostaglandin E1 analog, prostaglandin E2, a prostaglandin E2 analog, and mixtures thereof. A preferred cyclic lipid therapeutic agent within the scope of our invention is bimatoprost, a bimatoprost analog, and mixtures thereof.

The polymer matrix can be a biodegradable or a non-biodegradable polymer. The biodegradable polymer can be for example a polylactic acid, polyglycolic acid, polylactide-co-glycolide, a poly(polylactide-co-glycolide) [PLGA] copolymer and copolymers thereof, as well as derivatives of these polymers. Other suitable polymers to use can include poly caprolactones, and PLGA-PEG or PLA-PEG diblock or triblock polymers.

In our low temperature process for making an intraocular implant, the polymer can comprise from about 30% to about 95% by weight of the implant and the cyclic lipid therapeutic agent can comprise from about 5% to about 70% by weight of the implant. Notably, the potency of the cyclic lipid therapeutic agent released from the implant can be at least about 50% of its maximum potency.

A detailed embodiment of our low temperature process for making an intraocular implant can have the steps of: (a) combining a prostaglandin analog and a biodegradable polymer to form a mixture; (b) heating the mixture to a temperature between about 50° C. and about 80° C., and; (c) extruding the heated mixture, thereby making an implant suitable for intraocular use.

An alternate embodiment of our invention is a process for making an intraocular implant by firstly combining a cyclic lipid therapeutic agent, a first biodegradable polymer, and a second biodegradable polymer to form a mixture. Preferably, the first biodegradable polymer and the second biodegradable polymer are different polymers, the solubilities of the cyclic lipid therapeutic agent, the first biodegradable polymer, and the second biodegradable polymer are substantially similar, and, the melting point of the second biodegradable polymer is lower than the melt temperature of the first biodegradable polymer. The next step in this process is to heat the mixture made combining the cyclic lipid therapeutic agent, the first biodegradable polymer, and a second biodegradable polymer. The mixture is heated to the temperature which is lower than the melt temperature of the second biodegradable polymer. Advantageously, the temperature to which the mixture is heated is also lower than the temperature at which the cyclic lipid therapeutic agent exhibits substantial degradation. The third step in this process is to extrude the heated mixture to thereby making an implant suitable for intraocular use.

In this alternate embodiment of our invention the first biodegradable polymer can be for example a polylactic acid, polyglycolic acid, polylactide-co-glycolide, a poly(polylactide-co-glycolide) copolymer, and copolymers thereof. Additionally, the second biodegradable polymer can be any substituted poly lactide, poly glycolide, or poly(lactide-co-glycolide), any poly(caprolactone) or substituted derivative or any of the above, as well as any of the above polymers where a low molecular weight polyether is incorporated as a block with the polymer.

Significantly, the second biodegradable polymer functions as a cosolvent for the first biodegradable polymer and for the cyclic lipid therapeutic agent. This permits a solid solution of these three components to be formed when the mixture is heated to the melt temperature of the second biodegradable polymer. The second biodegradable polymer has a low melt temperature (i.e. between about 50° C. about 80° C.) and importantly has a solubility parameter which is similar to the solubility parameters of both the cyclic lipid therapeutic agent and the first biodegradable polymer. In particular, suitable second biodegradable polymers can include:

| Polymer | Solubility Parameter (δ) |
|---|---|
| decafluorobutane | 10.6 |
| Poly(isobutylene) | 16.2 |
| Poly(hexamethylene adipamide) | 13.6 |
| Poly Propylene | 18.0 |
| Poly Ethylene | 18.1 |
| Poly Vinyl Chloride | 21.4, | as well as other low molecular weight polymers, waxes, and long chain hydrocarbons that have softening points below about 80° C. and solubility parameters from about 12 to about 28 $(MPa)^{1/2}$.

Preferably, the solubilities of the cyclic lipid therapeutic agent, the first biodegradable polymer, and the second biodegradable polymer are all within about 10 $Mpa^{1/2}$ of each other. Additionally, the solubility parameters (solubilities) of the cyclic lipid therapeutic agent, the first biodegradable polymer, and the second biodegradable polymer are also preferably all within about 15 to 30 $Mpa^{1/2}$.

The first biodegradable polymer can comprises from about 30% to about 90% by weight of the implant, the second biodegradable polymer can comprises from about 50% to about 30% by weight of the implant, and the cyclic lipid therapeutic agent can comprise from about 5% to about 30% by weight of the implant.

A detailed embodiment of this alternate embodiment of our invention is a process for making an intraocular implant, the process comprising the steps of:
(a) combining:
  (i) a prostaglandin analog, wherein the prostaglandin analog comprises from about 5% to about 30% (and up to as much as 70%) by weight of the implant;
  (ii) a poly(lactide-co-glycolide) copolymer, wherein the poly(lactide-co-glycolide) comprises from about 30% to about 90% by weight of the implant.
and;
  (ii) a second biodegradable polymer to form a mixture, wherein the second biodegradable polymer comprises from about 5% to about 40% by weight of the implant, and wherein;
    (α) the a poly(lactide-co-glycolide) copolymer and the second biodegradable polymer are different polymers;
    (β) the solubilities of the prostaglandin analog, the poly(lactide-co-glycolide) copolymer, and the second biodegradable polymer are all within about 10 $Mpa^{1/2}$ of each other, and;
    (γ) the melt temperature of the second biodegradable polymer is lower than the melt temperature of the a poly(lactide-co-glycolide) copolymer, and is as well lower than the temperature at which the prostaglandin analog exhibits substantial degradation, or exhibits a potency less than about 50% of it's label strength;
(b) heating the mixture to the lower melt temperature of the second biodegradable polymer, so that the second biodegradable polymer can function as a solvent for the prostaglandin analog and for the a poly(lactide-co-glycolide) copolymer, and;
(c) extruding the heated mixture, thereby making an implant suitable for intraocular use.

Our invention also encompasses a method for treating an ocular condition using an implant made as set forth herein. The implant can release (such as release a therapeutically effective amount of) the cyclic lipid therapeutic agent for at least about one week after its insertion or implantation into an intraocular location. The cyclic lipid therapeutic agent can be a non-acid cyclic lipid therapeutic agent.

Importantly, the implant can have an average greatest dimension in a range of from about 0.4 mm to about 12 mm.

The cyclic lipid therapeutic agent can have the following formula (I)

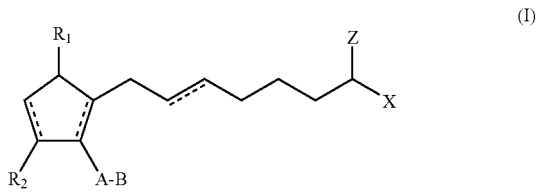

(I)

wherein the dashed bonds represent a single or double bonds which can be in the cis or trans configuration, A is an alkyene or alkenylene radical having from two to six carbon atoms, which radical may be interrupted by one or more oxide radicals and substituted with one or more hydroxy, oxo, alkoxy or alkycarboxyl groups wherein said alkyl radical comprises from one to six carbon atoms; B is a cycloalkyl radical having from three to seven carbon atoms, or an aryl radical, selected from the group consisting of hydrocarbyl aryl and heteroaryl radicals having from four to ten carbon atoms wherein the heteroatom is selected from the group consisting of nitrogen, oxygen and sulfur atoms; X is a radical selected from the group consisting of hydrogen, a lower alkyl radical having from one to six carbon atoms, $R^5$—C(=O)— or $R^5$—O—C(=O)— wherein $R^5$ is a lower alkyl radical having from one to six carbon atoms; Z is =O or represents 2 hydrogen radicals; one of $R_1$ and $R^2$ is =O, —OH or a —O—C(=O)—$R^6$ group, and the other one is —OH or —O—C(=O)—$R^6$, or $R^1$ is =O and $R^2$ is H, wherein $R^6$ is a saturated or unsaturated acyclic hydrocarbon group having from 1 to about 20 carbon atoms, or —$(CH_2)_m R^7$ wherein m is 0-10, and $R^7$ is cycloalkyl radical, having from three to seven carbon atoms, or a hydrocarbyl aryl or heteroaryl radical, as defined above, or a pharmaceutically acceptable salt thereof, provided however that when B is not substituted with a pendant heteroatom-containing radical and Z is =O, then X is not —$OR^4$.

Alternately, the cyclic lipid therapeutic agent can have the following formula (II)

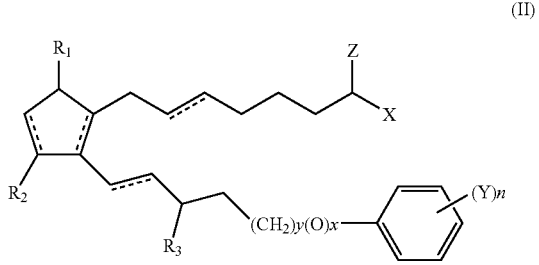

(II)

wherein y is 0 or 1, x is 0 or 1 and x+y re not both 1, Y is a radical selected from the group consisting of alkyl, halo, nitro, amino, thiol, hydroxy, alkyloxy, alkylcarboxy and halo substituted alkyl, wherein said alkyl radical comprises from one to six carbon atoms, n is O or an integer of from 1 to 3 and R3 is =O, —OH or —O—C(=O)$R^6$.

Alternately, the cyclic lipid therapeutic agent can comprise a compound having the following formula (III)

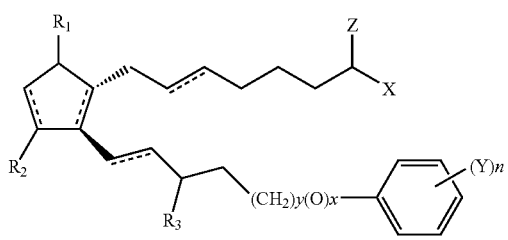

(III)

wherein hatched lines indicate the α configuration and solid triangles indicate the β configuration.

Alternately, the cyclic lipid therapeutic agent can comprises a compound having the following formula (IV)

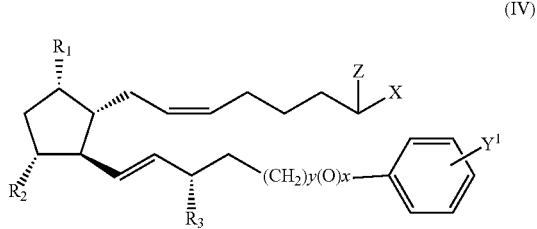

(IV)

wherein $Y^1$ is Cl or trifluoromethyl.

Alternately, the cyclic lipid therapeutic agent can comprise a compound having the following formula (V)

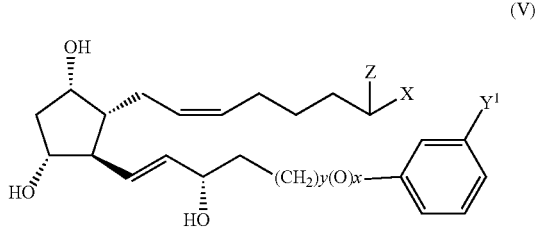

(V)

and the 9- and/or 11- and/or 15-esters, thereof. Z can be O and X can be selected from the group consisting of $NH_2$ or $OCH_3$. Alternately, Y can be 0, Z can be O and X can be selected from the group consisting of alkoxy and amido radicals.

Alternately, the cyclic lipid therapeutic agent comprises a compound selected from the group consisting of:
a) cyclopentane heptenol-5-cis-2-(3α-hydroxy-5-phenyl-1-trans-pentenyl)-3,5-dihydroxy, [1α, 2β, 3α, 5α];
b) cyclopentane heptenamide-5-cis-2-(3α-hydroxy-5-phenyl-1-trans-pentenyl)-3,5-dihydroxy, [1α, 2β, 3α, 5α];
c) cyclopentane N,N-dimethylheptenamide-5-cis-2-(3α-hydroxy-5-phenyl-1-trans-penten-yl)-3,5-dihydroxy, [1α, 2β, 3α, 5α];
d) cyclopentane heptenyl methoxide-5-cis-2-(3α-hydroxy-5-phenyl-1-trans-pentenyl)-3,5-dihydroxy, [1α, 2β, 3α, 5α];
e) cyclopentane heptenyl ethoxide-5-cis-2-(3α-hydroxy-4-meta-chloro-phenoxy-1-trans-butenyl)-3,5-dihydroxy, [1α, 2β, 3α, 5α];
f) cyclopentane heptenylamide-5-cis-2-(3α-hydroxy-4-meta-chloro-phenox-y-1-trans-butenyl)-3,5-dihydroxy, [1α, 2β, 3α, 5α];
g) cyclopentane heptenylamide-5-cis-2-(3α-hydroxy-4-meta-tr-ifluoromethyl-phenoxy-1-trans-butenyl)-3,5-dihydroxy, [1α, 2β, 3α, 5α];
h) cyclopentane N-isopropyl hepteneamide-5-cis-2-(3α-hydroxy-5-phenyl-1-trans-pentenyl)-3,5-dihydroxy, [1α, 2β, 3α, 5α];
i) cyclopentane N-ethyl heptenamide-5-cis-2-(3α-hydroxy-5-phenyl-1-trans-pentenyl)-3,5-dihydroxy, [1α, 2β, 3α, 5α];
j) cyclopentane N-methyl heptenamide-5-cis-2-(3α-hydroxy-5-phenyl-1-trans-pentenyl)-3,5-dihydroxy, [1α, 2β, 3α, 5α];
k) cyclopentane heptenol-5-cis-2-(3α-hydroxy-4-meta-chlorophenoxy-1-trans-butenyl)-3,5-dihydroxy, [1α, 2β, 3α, 5α];
l) cyclopentane heptenamide-5-cis-2-(3α-hydroxy-4-m-chlorophenoxy-1-trans-butenyl)-3,5-dihydroxy, [1α, 2β, 3α, 5α], and
m) cyclopentane heptenol-5-cis-2-(3α-hydroxy-5-phenyl-pentyl)3,5-dihydroxy, [1α, 2β, 3α, 5α].

Alternately, the cyclic lipid therapeutic agent can comprise a compound having the following formula (VI)

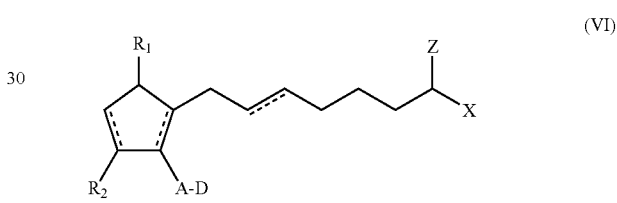

(VI)

wherein the dashed bonds represent a single or double bonds which can be in the cis or trans configuration, A is an alkyene or alkenylene radical having from two to six carbon atoms, which radical may be interrupted by one or more oxide radicals and substituted with one or more hydroxy, oxo, alkoxy or alkycarboxyl groups wherein said alkyl radical comprises from one to six carbon atoms; D is a branched or unbranched alkyl or heteroalkyl radical of from two to 10 carbon atoms, a cycloalkyl radical having from three to seven carbon atoms, or an aryl radical, selected from the group consisting of hydrocarbyl aryl and heteroaryl radicals having from four to ten carbon atoms wherein the heteroatom is selected from the group consisting of nitrogen, oxygen and sulfur atoms; X is a radical selected from the group consisting of hydrogen, a lower alkyl radical having from one to six carbon atoms, $R^5$—C(=O)— or $R^5$—O—C(=O)— wherein $R^5$ is a lower alkyl radical having from one to six carbon atoms; Z is =O or represents 2 hydrogen radicals; one of $R_1$ and $R^2$ is =O, —OH or a —O—C(=O)—$R^6$ group, and the other one is —OH or —O—C(=O)—$R^6$, or $R^1$ is =O and $R^2$ is H, wherein $R^6$ is a saturated or unsaturated acyclic hydrocarbon group having from 1 to about 20 carbon atoms, or —$(CH_2)_m$ $R^7$ wherein m is 0-10, and $R^7$ is cycloalkyl radical, having from three to seven carbon atoms, or a hydrocarbyl aryl or heteroaryl radical, as defined above, or a pharmaceutically acceptable salt thereof.

Alternately, the cyclic lipid therapeutic agent can comprise a compound having the following formula (VII)

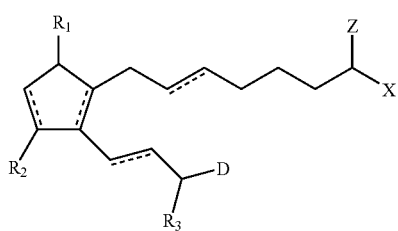

(VII)

Alternately, the cyclic lipid therapeutic agent can comprise a compound having the following formula (VII)

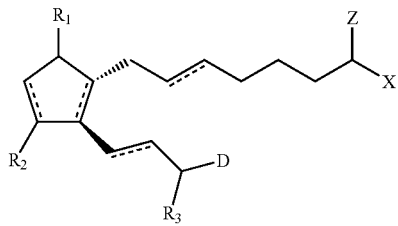

(VIII)

wherein hatched lines indicate the α configuration and the solid triangles comprise the β configuration.

Alternately, the cyclic lipid therapeutic agent can comprise a compound having the following formula (IX)

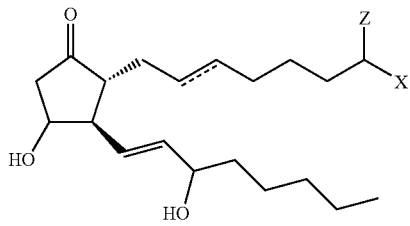

(IX)

Alternately, the cyclic lipid therapeutic agent can comprise a compound having the following formula (X)

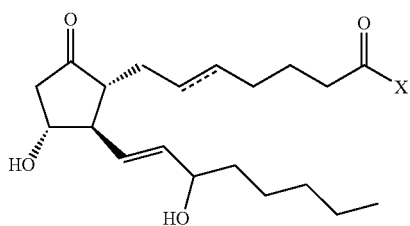

(X)

Alternately, the cyclic lipid therapeutic agent can comprise a compound having the following formula (XI).

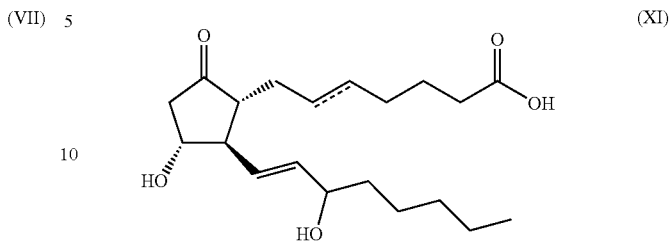

(XI)

Additional aspects and advantages of the present invention are set forth in the following description and claims, particularly when considered in conjunction with the accompanying drawings.

DRAWINGS

The following drawings illustrate features and aspects of our invention.

FIG. 1 is a bar graph which shows the effect of decreasing temperature (the x axis) on the potency (the y axis) of the bimatoprost released from extruded implants made at different temperatures.

FIG. 2 is a graph which shows the total amount of bimatoprost released (the y-axis) over a period of fifty days (the x axis) from the FIG. 1 extruded implant made at 57° C.

FIG. 3 is a graph which shows the daily amount of bimatoprost released (the y axis) from the FIG. 2 implant over a period of 50 days (the x axis).

DESCRIPTION

Our invention is based on the discovery of a new process for making sustained release intraocular implants. Implants made by our new process can comprise a therapeutic agent and a polymer. The polymer functions as a carrier from which the therapeutic agent is released in vivo. The therapeutic agent and the polymer are heated and extruded to form an implant suitable for intraocular use. Preferably, the polymer has a $T_g$ which is below the temperature at which the therapeutic agent loses a substantial amount (i.e. 50% or more) of its potency. If the polymer (the first polymer) has a $T_g$ which is above the temperature at which the therapeutic agent loses a substantial amount of its potency, the implant can be made by a process which entails adding a cosolvent to an unheated mixture of the therapeutic agent and the first polymer. The cosolvent can also be a polymer (the second polymer).

The cosolvent must have two important properties. First the cosolvent must have a solubility (i.e. a solubility parameter) which is similar to the solubilities (i.e. the solubility parameters) of both the therapeutic agent and the first polymer. Clearly, this requires that the solubility of the therapeutic agent be similar to the solubility of the first polymer. Upon selection of therapeutic agent, first polymer and cosolvent with similar solubilities, heating these three implant constituents so as to melt the cosolvent will result in solubilization of the therapeutic agent and the first polymer in the cosolvent.

The second important property of the co-solvent is that the co-solvent has a softening point which is below the temperature at which the therapeutic agent loses a substantial amount of its potency. Thus, when according to our process the therapeutic agent, the first polymer and the co-solvent are mixed and then heated to the melt temperature of the cosolvent, the cosolvent solubilizes the therapeutic agent and the first polymer and does so without undue loss of potency of the therapeutic agent. Where the cosolvent is itself a polymer (the second polymer), the cosolvent solubilizes the therapeutic agent and the first polymer in the form of a solid solution.

A sustained release implant (implanted for example in the subconjuntiva of the eye) can remove the need for daily administration of an anti-hypertensive active agent by providing a controlled release of the hypotensive agent over an extended period of time. The antihypertensive agent can be a prostaglandin analog, such as a bimatoprost. A bimatoprost containing polymeric implant can be an effective method of delivering a controlled dose of bimatoprost to the eye over an extended time. As described herein, controlled and sustained administration of a therapeutic agent through the subconjunctival administration of one or more implants can be used to treat ocular conditions of the anterior and/or posterior segment of the eye. The implants comprise a pharmaceutically acceptable polymeric composition and are formulated to release one or more pharmaceutically active agents, such as a cyclic lipid, or other intraocular pressure lowering or neuroprotective agent, over an extended period of time. The implants are effective to provide a therapeutically effective dosage of the agent or agents to a region of the eye to treat or prevent one or more undesirable ocular conditions. Thus with a single implant administration cyclic lipid therapeutic agents can be made available at the site where they are needed and will be maintained for an extended period of time, rather than subjecting the patient to repeated injections or repeated administration of topical drops.

The implants of the present invention comprise a therapeutic component and a drug release-sustaining component associated with the therapeutic component. In accordance with the present invention, the therapeutic component comprises, consists essentially of, or consists of, a cyclic lipid therapeutic agent. The drug release sustaining component is associated with the therapeutic component to sustain release of an effective amount of the cyclic lipid therapeutic agent into an eye in which the implant is placed. The amount of the cyclic lipid therapeutic agent is released into the eye for a period of time greater than about one week after the implant is implanted or inserted in the eye of a patient, and is effective in treating or reducing a symptom of an ocular condition, such as ocular hypertension or a retinal degeneration.

DEFINITIONS

"About" means that the number, range, value or parameter so qualified encompasses ten percent more and ten percent less of the number, range, value or parameter.

"Therapeutic component" means that portion of an implant other than the polymer matrix comprising one or more therapeutic agents or substances used to treat an ocular condition. The therapeutic component can be a discrete region of an implant, or it may be homogenously distributed throughout the implant. The therapeutic agents of the therapeutic component comprise at least one cyclic lipid and are typically ophthalmically acceptable, and are provided in a form that does not cause significant adverse reactions when the implant is placed in an eye.

"Cyclic lipid therapeutic agent" means that portion of an intraocular implant which comprises one or more cyclic lipids having ocular therapeutic activity, including, without limitation, a prostaglandin, prostaglandin analog, prostaglandin derivative, prostamide, prostamide analog, and a prostamide derivative that is effective in providing an ophthalmic therapeutic effect, such as, without limitation, reducing or maintaining a reduced intraocular pressure in a hypertensive eye, or providing to the retina of an eye an effective amount of a cyclic lipid therapeutic agent having neuroprotective activities. Cyclic lipids having anti-glaucoma activity can be identified by applying the cyclic lipid to an eye with increased intraocular pressure, and evaluating whether the intraocular pressure decreases after the application. Cyclic lipids having neuroprotective activity may be identified by, for example, intravitreal administration of the cyclic lipid to an eye having a neurodegenerative disorder such as ARMD, and evaluating whether the neurodegeneration is slowed or halted, or whether visual acuity has increased.

"Drug release sustaining component" means that portion of an implant that is effective to provide a sustained release of the therapeutic agents from the implant. A drug release sustaining component can be a biodegradable polymer matrix, or it can be a coating covering a core region of the implant that comprises a therapeutic component.

"Associated with" means mixed with, dispersed within, coupled to, covering, or surrounding.

"Ocular region" or "ocular site" means any area of the eyeball, including the anterior and posterior segment of the eye, and which generally includes, but is not limited to, any functional (e.g., for vision) or structural tissues found in the eyeball, or tissues or cellular layers that partly or completely line the interior or exterior of the eyeball. Specific examples of areas of the eyeball in an ocular region include the anterior chamber, the posterior chamber, the vitreous cavity, the choroid, the suprachoroidal space, the conjunctiva, the subconjunctival space, the episcleral space, the intracorneal space, the epicorneal space, the sclera, the pars plana, surgically-induced avascular regions, the macula, and the retina.

"Ocular condition" means a disease, ailment or condition which affects or involves the eye or one of the parts or regions of the eye. Broadly speaking the eye includes the eyeball and the tissues and fluids which constitute the eyeball, the periocular muscles (such as the oblique and rectus muscles) and the portion of the optic nerve which is within or adjacent to the eyeball. An anterior ocular condition is a disease, ailment or condition which affects or which involves an anterior (i.e. front of the eye) ocular region or site, such as a periocular muscle, an eye lid or an eye ball tissue or fluid which is located anterior to the posterior wall of the lens capsule or ciliary muscles. Thus, an anterior ocular condition primarily affects or involves the conjunctiva, the cornea, the anterior chamber, the iris, the posterior chamber (behind the retina but in front of the posterior wall of the lens capsule), the lens or the lens capsule and blood vessels and nerve which vascularize or innervate an anterior ocular region or site.

Thus, an anterior ocular condition can include a disease, ailment or condition, such as for example, aphakia; pseudophakia; astigmatism; blepharospasm; cataract; conjunctival diseases; conjunctivitis; corneal diseases; corneal ulcer; dry eye syndromes; eyelid diseases; lacrimal apparatus diseases; lacrimal duct obstruction; myopia; presbyopia; pupil disorders; refractive disorders and strabismus. Glaucoma can also be considered to be an anterior ocular condition because a clinical goal of glaucoma treatment can be to reduce a hypertension of aqueous fluid in the anterior chamber of the eye (i.e. reduce intraocular pressure).

A posterior ocular condition is a disease, ailment or condition which primarily affects or involves a posterior ocular region or site such as choroid or sclera (in a position posterior to a plane through the posterior wall of the lens capsule), vitreous, vitreous chamber, retina, optic nerve (i.e. the optic disc), and blood vessels and nerves which vascularize or innervate a posterior ocular region or site. Thus, a posterior ocular condition can include a disease, ailment or condition, such as for example, acute macular neuroretinopathy; Behcet's disease; choroidal neovascularization; diabetic uveitis; histoplasmosis; infections, such as fungal or viral-caused infections; macular degeneration, such as acute macular degeneration, non-exudative age related macular degeneration and exudative age related macular degeneration; edema, such as macular edema, cystoid macular edema and diabetic macular edema; multifocal choroiditis; ocular trauma which affects a posterior ocular site or location; ocular tumors; retinal disorders, such as central retinal vein occlusion, diabetic retinopathy (including proliferative diabetic retinopathy), proliferative vitreoretinopathy (PVR), retinal arterial occlusive disease, retinal detachment, uveitic retinal disease; sympathetic opthalmia; Vogt Koyanagi-Harada (VKH) syndrome; uveal diffusion; a posterior ocular condition caused by or influenced by an ocular laser treatment; posterior ocular conditions caused by or influenced by a photodynamic therapy, photocoagulation, radiation retinopathy, epiretinal membrane disorders, branch retinal vein occlusion, anterior ischemic optic neuropathy, non-retinopathy diabetic retinal dysfunction, retinitis pigmentosa, and glaucoma. Glaucoma can be considered a posterior ocular condition because the therapeutic goal is to prevent the loss of or reduce the occurrence of loss of vision due to damage to or loss of retinal cells or optic nerve cells (i.e. neuroprotection).

"Biodegradable polymer" means a polymer or polymers which degrade in vivo, and wherein erosion of the polymer or polymers occurs concurrent with or subsequent to release of the therapeutic agent. Specifically, hydrogels such as methylcellulose which act to release drug through polymer swelling are specifically excluded from the term "biodegradable polymer". The terms "biodegradable" and "bioerodible" are equivalent and are used interchangeably herein. A biodegradable polymer may be a homopolymer, a copolymer, or a polymer comprising more than two different polymeric units.

"Treat", "treating", or "treatment" means a reduction or resolution or prevention of an ocular condition, ocular injury or damage, or to promote healing of injured or damaged ocular tissue. A treatment is usually effective to reduce at least one symptom of an ocular condition, ocular injury or damage.

"Therapeutically effective amount" means the level or amount of agent needed to treat an ocular condition, or reduce or prevent ocular injury or damage without causing significant negative or adverse side effects to the eye or a region of the eye. In view of the above, a therapeutically effective amount of a therapeutic agent, such as a cyclic lipid, is an amount that is effective in reducing at least one symptom of an ocular condition.

Implants have been developed which can release drug loads over various time periods. These implants when inserted into the subconjunctival space of an eye provide therapeutic levels of a cyclic lipid for extended periods of time (e.g., for about 1 week or more). The disclosed implants are effective in treating ocular conditions, such as ocular conditions associated with elevated intraocular pressure, and more specifically in reducing at least one symptom of glaucoma.

Processes for making implants have also been developed. For example, the present invention encompasses therapeutic polymeric implants and processes for making and using such implants. In one embodiment of the present invention, an implant comprises a biodegradable polymer matrix. The biodegradable polymer matrix is one type of a drug release sustaining component. The biodegradable polymer matrix is effective in forming a biodegradable implant. The biodegradable implant comprises a cyclic lipid therapeutic agent associated with the biodegradable polymer matrix. The matrix degrades at a rate effective to sustain release of an amount of the cyclic lipid therapeutic agent for a time greater than about one week from the time in which the implant is placed in ocular region or ocular site, such as the subconjunctival space of an eye.

The prostamide having a name cyclopentane N-ethyl heptenamide-5-cis2-cis-2-(3α-hydroxy-5-phenyl-1-trans-pentenyl)-3,5-dihydroxy, [1α,2β,3α,5α], and derivatives, analods, and/or esters thereof, is particularly preferred in this aspect of the invention. This compound is also known as bimatoprost and is available in a topical ophthalmic solution under the tradename, Lumigan® (Allergan, Inc., California).

The Implant can comprise a therapeutic component which comprises, consists essentially of, or consists of bimatoprost, a salt thereof, or mixtures thereof. The cyclic lipid therapeutic agent can be in a liquid, derivatized, particulate, or powder form and it may be entrapped by the biodegradable polymer matrix. Usually, cyclic lipid particles will have an effective average size less than about 3000 nanometers. In certain implants, the particles may have an effective average particle size about an order of magnitude smaller than 3000 nanometers. For example, the particles may have an effective average particle size of less than about 500 nanometers. In additional implants, the particles may have an effective average particle size of less than about 400 nanometers, and in still further embodiments, a size less than about 200 nanometers.

The cyclic lipid therapeutic agent of the implant is preferably from about 10% to 90% by weight of the implant. More preferably, the cyclic lipid therapeutic agent is from about 20% to about 80% by weight of the implant. In a preferred embodiment, the cyclic lipid therapeutic agent comprises about 20% by weight of the implant (e.g., 15%-25%). In another embodiment, the cyclic lipid therapeutic agent comprises about 50% by weight of the implant.

Suitable polymeric materials or compositions for use in the implant include those materials that are biocompatible with the eye so as to cause no substantial interference with the functioning or physiology of the eye. Such materials preferably are at least partially and more preferably substantially completely biodegradable or bioerodible.

Examples of useful polymeric materials include, without limitation, such materials derived from and/or including organic esters and organic ethers, which when degraded result in physiologically acceptable degradation products, including the monomers. Also, polymeric materials derived from and/or including, anhydrides, amides, orthoesters and the like, by themselves or in combination with other monomers, may also find use. The polymeric materials may be addition or condensation polymers, advantageously condensation polymers. The polymeric materials may be cross-linked or non-cross-linked, for example not more than lightly cross-linked, such as less than about 5%, or less than about 1% of the polymeric material being cross-linked. For the most part, besides carbon and hydrogen, the polymers will include at least one of oxygen and nitrogen, advantageously oxygen. The oxygen may be present as oxy, e.g. hydroxy or ether, carbonyl, e.g. nonoxo-carbonyl, such as carboxylic acid ester, and the like. The nitrogen may be present as amide, cyano and amino. The polymers set forth in Heller, Biodegradable Polymers in Controlled Drug Delivery, In: CRC Critical Reviews in Therapeutic Drug Carrier Systems, Vol. 1, CRC Press, Boca Raton, Fla. 1987, pp 39-90, which describes encapsulation for controlled drug delivery, may find use in the present implant.

Of additional interest are polymers of hydroxyaliphatic carboxylic acids, either homopolymers or copolymers, and polysaccharides. Polyesters of interest include polymers of D-lactic acid, L-lactic acid, racemic lactic acid, glycolic acid, polycaprolactone, and combinations thereof. Generally, by employing the L-lactate or D-lactate, a slowly eroding polymer or polymeric material is achieved, while erosion is substantially enhanced with the lactate racemate.

Among the useful polysaccharides are, without limitation, calcium alginate, and functionalized celluloses, particularly carboxymethylcellulose esters characterized by being water insoluble, a molecular weight of about 5 kD to 500 kD, for example. Other polymers of interest include, without limitation, polyvinyl alcohol, polyesters, polyethers and combinations thereof which are biocompatible and may be biodegradable and/or bioerodible.

Some preferred characteristics of the polymers or polymeric materials for use in the present invention may include biocompatibility, compatibility with the therapeutic component, ease of use of the polymer in making the drug delivery systems of the present invention, a half-life in the physiological environment of at least about 6 hours, preferably greater than about one day, and water insolubility.

The biodegradable polymeric materials which are included to form the matrix are desirably subject to enzymatic or hydrolytic instability. Water soluble polymers may be cross-linked with hydrolytic or biodegradable unstable cross-links to provide useful water insoluble polymers. The degree of stability can be varied widely, depending upon the choice of monomer, whether a homopolymer or copolymer is employed, employing mixtures of polymers, and whether the polymer includes terminal acid groups.

Equally important to controlling the biodegradation of the polymer and hence the extended release profile of the implant is the relative average molecular weight of the polymeric composition employed in the implant. Different molecular weights of the same or different polymeric compositions may be included in the implant to modulate the release profile. In certain implants, the relative average molecular weight of the polymer will range from about 9 to about 500 kD, usually from about 10 to about 300 kD, and more usually from about 12 to about 100 kD.

In some implants copolymers of glycolic acid and lactic acid are used, where the rate of biodegradation is controlled by the ratio of glycolic acid to lactic acid. The most rapidly degraded copolymer has roughly equal amounts of glycolic acid and lactic acid. Homopolymers, or copolymers having ratios other than equal, are more resistant to degradation. The ratio of glycolic acid to lactic acid will also affect the brittleness of the implant. The percentage of polylactic acid in the polylactic acid polyglycolic acid (PLGA) copolymer can be 0-100%, preferably about 15-85%, more preferably about 35-65%. In some implants a 50/50 PLGA copolymer is used.

The biodegradable polymer matrix of the subconjunctival implant can comprise a mixture of two or more biodegradable polymers. For example, the implant can comprise a mixture of a first biodegradable polymer and a different second biodegradable polymer. One or more of the biodegradable polymers can have terminal acid groups.

Release of a drug from an erodible polymer is the consequence of several mechanisms or combinations of mechanisms. Some of these mechanisms include desorption from the implant's surface, dissolution, diffusion through porous channels of the hydrated polymer and erosion. Erosion can be bulk or surface or a combination of both. As discussed herein, the matrix of the implant can release drug at a rate effective to sustain release of an amount of the prostamide component for more than one week after implantation into an eye. In certain implants therapeutic amounts of the cyclic lipid therapeutic agent are released for no more than about 30-35 days after administration to the subconjunctival space. For example, an implant may comprise bimatoprost, and the matrix of the implant degrades at a rate effective to sustain release of a therapeutically effective amount of bimatoprost for about one month after being placed under the conjunctiva. As another example, the implant may comprise bimatoprost, and the matrix releases drug at a rate effective to sustain release of a therapeutically effective amount of bimatoprost for more than forty days, such as for about six months.

One example of the biodegradable implant comprises a cyclic lipid therapeutic agent associated with a biodegradable polymer matrix, which comprises a mixture of different biodegradable polymers. At least one of the biodegradable polymers is a polylactide having a molecular weight of about 63.3 kD. A second biodegradable polymer is a polylactide having a molecular weight of about 14 kD. Such a mixture is effective in sustaining release of a therapeutically effective amount of the cyclic lipid therapeutic agent for a time period greater than about one month from the time the implant are placed administered under the conjuctiva.

Another example of a biodegradable implant comprises a cyclic lipid therapeutic agent associated with a biodegradable polymer matrix, which comprises a mixture of different biodegradable polymers, each biodegradable polymer having an inherent viscosity from about 0.16 dL/g to about 1.0 dL/g. For example, one of the biodegradable polymers may have an inherent viscosity of about 0.3 dl/g. A second biodegradable polymer may have an inherent viscosity of about 1.0 dl/g. Additional implant may comprise biodegradable polymers that have an inherent viscosity between about 0.2 dl/g and 0.5 dl/g. The inherent viscosities identified above may be determined in chloroform, 0.1% at 25° C.

One particular implant formulation comprises bimatoprost associated with a combination of two different polylactide polymers. The bimatoprost is present in about 20% by weight of the implant. One polylactide polymer has a molecular weight of about 14 kD and an inherent viscosity of about 0.3 dl/g, and the other polylactide polymer has a molecular weight of about 63.3 kD and an inherent viscosity of about 1.0 dl/g. The two polylactide polymers are present in the implant in a 1:1 ratio. Such an implant may be effective in releasing the bimatoprost for more than two months.

The release of the cyclic lipid therapeutic agent from the implant into the subconjuctiva can include an initial burst of release followed by a gradual increase in the amount of the cyclic lipid therapeutic agent released, or the release can include an initial delay in release of the prostamide component followed by an increase in release. When the implant is substantially completely degraded, the percent of the cyclic lipid therapeutic agent that has been released is about one hundred. The implant disclosed herein do not completely release, or release about 100% of the cyclic lipid therapeutic agent, until after about one week of being placed in an eye.

It can be desirable to provide a relatively constant rate of release of the cyclic lipid therapeutic agent from the implant over the life of the implant. For example, it may be desirable for the cyclic lipid therapeutic agent to be released in amounts from about 0.01 µg to about 2 µg per day for the life of the implant. However, the release rate can change to either increase or decrease depending on the formulation of the biodegradable polymer matrix. In addition, the release profile of the prostamide component may include one or more linear portions and/or one or more non-linear portions. Preferably, the release rate is greater than zero once the implant has begun to degrade or erode.

The implant can be monolithic, i.e. having the active agent or agents homogenously distributed through the polymeric matrix, or encapsulated, where a reservoir of active agent is encapsulated by the polymeric matrix. Due to ease of manufacture, monolithic implants are usually preferred over encapsulated forms. However, the greater control afforded by the encapsulated implant may be of benefit in some circumstances, where the therapeutic level of the drug falls within a narrow window. In addition, the therapeutic component, including the cyclic lipid therapeutic agent, can be distributed in a non-homogenous pattern in the matrix. For example, the implant may include a portion that has a greater concentration of the cyclic lipid therapeutic agent relative to a second portion of the implant.

The implants disclosed herein can have a size of between about 0.1 mm and about 12 mm. For needle (syringe)-injected implant, the implant can have any appropriate dimensions so long as the longest dimension of the implant permits the implant to move through a canula of the needle. This is generally not a problem in the administration of implant. The subconjunctival space in humans is able to accommodate relatively large volumes of implant.

The total weight of an implant is from about 0.1 mg to about 5 mg. For example, a single subconjunctival implant (human patient) can weigh between 0.1 to 2 mg, including the incorporated therapeutic component. The dosage of the therapeutic component in the implant is generally in the range of from about 55% to about 95% by weight of the implant weight. Thus, implant can be prepared where the center may be of one material and the surface may have one or more layers of the same or a different composition, where the layers may be cross-linked, or of a different molecular weight, different density or porosity, or the like. For example, where it is desirable to quickly release an initial bolus of drug, the center of the implant may be a polylactate coated with a polylactate-polyglycolate copolymer, so as to enhance the rate of initial degradation. Alternatively, the center may be polyvinyl alcohol coated with polylactate, so that upon degradation of the polylactate exterior the center would dissolve and be rapidly washed out of the eye.

The implant can be of any geometry (excluding microspheres and microparticles). The upper limit for the implant size will be determined by factors such as toleration for the implant, size limitations on insertion, desired rate of release, ease of handling, etc. The size and form of the implant can also be used to control the rate of release, period of treatment, and drug concentration at the site of implantation. Larger implants will deliver a proportionately larger dose, but depending on the surface to mass ratio, may have a slower release rate. The particular size and geometry of the implant are chosen to suit the activity of the active agent and the location of its target tissue.

The proportions of the cyclic lipid therapeutic agent, polymer, and any other modifiers can be empirically determined by formulating several implants with varying average proportions. A USP approved method for dissolution or release test can be used to measure the rate of release. For example, using an infinite sink method, a weighed sample of the implant is added to a measured volume of a solution containing 0.01 M phosphate buffered saline (PBS) pH 7.4 at 37° C., where the solution volume will be such that the drug concentration is after release is less than 5% of saturation. The mixture is maintained at 37° C. and stirred slowly to maintain the implant in suspension. The appearance of the dissolved drug as a function of time may be followed by various methods known in the art, such as spectrophotometrically, HPLC, mass spectroscopy, etc. until the absorbance becomes constant or until greater than 90% of the drug has been released.

In addition to the cyclic lipid therapeutic agent included in the implant disclosed herein, the implant can also include one or more additional ophthalmically acceptable therapeutic agents. For example, the implant can include one or more antihistamines, one or more antibiotics, one or more beta blockers, one or more steroids, one or more antineoplastic agents, one or more immunosuppressive agents, one or more antiviral agents, one or more antioxidant agents, and mixtures thereof. Additional pharmacologic or therapeutic agents which may find use in the present systems, include, without limitation, those disclosed in U.S. Pat. No. 4,474,451, columns 4-6 and U.S. Pat. No. 4,327,725, columns 7-8.

Examples of antihistamines include, and are not limited to, loradatine, hydroxyzine, diphenhydramine, chlorpheniramine, brompheniramine, cyproheptadine, terfenadine, clemastine, triprolidine, carbinoxamine, diphenylpyraline, phenindamine, azatadine, tripelennamine, dexchlorpheniramine, dexbrompheniramine, methdilazine, and trimprazine doxylamine, pheniramine, pyrilamine, chiorcyclizine, thonzylamine, and derivatives thereof.

Examples of antibiotics include without limitation, cefazolin, cephradine, cefaclor, cephapirin, ceftizoxime, cefoperazone, cefotetan, cefutoxime, cefotaxime, cefadroxil, ceftazidime, cephalexin, cephalothin, cefamandole, cefoxitin, cefonicid, ceforanide, ceftriaxone, cefadroxil, cephradine, cefuroxime, ampicillin, amoxicillin, cyclacillin, ampicillin, penicillin G, penicillin V potassium, piperacillin, oxacillin, bacampicillin, cloxacillin, ticarcillin, azlocillin, carbenicillin, methicillin, nafcillin, erythromycin, tetracycline, doxycycline, minocycline, aztreonam, chloramphenicol, ciprofloxacin hydrochloride, clindamycin, metronidazole, gentamicin, lincomycin, tobramycin, vancomycin, polymyxin B sulfate, colistimethate, colistin, azithromycin, augmentin, sulfamethoxazole, trimethoprim, and derivatives thereof.

Examples of beta blockers include acebutolol, atenolol, labetalol, metoprolol, propranolol, timolol, and derivatives thereof. Examples of steroids include corticosteroids, such as cortisone, prednisolone, flurometholone, dexamethasone, medrysone, loteprednol, fluazacort, hydrocortisone, prednisone, betamethasone, prednisone, methylprednisolone, riamcinolone hexacatonide, paramethasone acetate, diflorasone, fluocinonide, fluocinolone, triamcinolone, derivatives thereof, and mixtures thereof.

Examples of antineoplastic agents include adriamycin, cyclophosphamide, actinomycin, bleomycin, duanorubicin, doxorubicin, epirubicin, mitomycin, methotrexate, fluorouracil, carboplatin, carmustine (BCNU), methyl-CCNU, cisplatin, etoposide, interferons, camptothecin and derivatives thereof, phenesterine, taxol and derivatives thereof, taxotere and derivatives thereof, vinblastine, vincristine, tamoxifen, etoposide, piposulfan, cyclophosphamide, and flutamide, and derivatives thereof.

Examples of immunosuppressive agents include cyclosporine, azathioprine, tacrolimus, and derivatives thereof. Examples of antiviral agents include interferon gamma, zidovudine, amantadine hydrochloride, ribavirin, acyclovir, valciclovir, dideoxycytidine, phosphonoformic acid, ganciclovir, and derivatives thereof.

Examples of antioxidant agents include ascorbate, alpha-tocopherol, mannitol, reduced glutathione, various carotenoids, cysteine, uric acid, taurine, tyrosine, superoxide dismutase, lutein, zeaxanthin, cryotpxanthin, astazanthin, lycopene, N-acetyl-cysteine, carnosine, gamma-glutamyl-cysteine, quercitin, lactoferrin, dihydrolipoic acid, citrate, Ginkgo Biloba extract, tea catechins, bilberry extract, vitamins E or esters of vitamin E, retinyl palmitate, and derivatives thereof.

Other therapeutic agents include squalamine, carbonic anhydrase inhibitors, alpha-2 adrenergic receptor agonists, antiparasitics, antifungals, and derivatives thereof. The amount of active agent or agents employed in the implant, individually or in combination, will vary widely depending on the effective dosage required and the desired rate of release from the implant. Usually the agent will be at least about 1, more usually at least about 10 weight percent of the implant, and usually not more than about 80, more usually not more than about 40 weight percent of the implant.

Some of the present implants may comprise a cyclic lipid therapeutic agent that comprises a combination of two or more different cyclic lipid derivatives. One implant or dosage of implant may comprise a combination of bimatoprost and latanoprost. Another implant or dosage of implant may comprise a combination of bimatoprost and travoprost.

As discussed herein, the present implant can comprise additional therapeutic agents. For example, one implant or dosage of implant may comprise a combination of bimatoprost and a beta-adrenergic receptor antagonist. More specifically, the implant or dosage of implant may comprise a combination of bimatoprost and Timolol®. Or, an implant or dosage of implant may comprise a combination of bimatoprost and a carbonic anyhdrase inhibitor. For example, the implant or dosage of implant may comprise a combination of bimatoprost and dorzolamide (Trusopt®).

In addition to the therapeutic component, the implant disclosed herein can include or may be provided in compositions that include effective amounts of buffering agents, preservatives and the like. Suitable water soluble buffering agents include, without limitation, alkali and alkaline earth carbonates, phosphates, bicarbonates, citrates, borates, acetates, succinates and the like, such as sodium phosphate, citrate, borate, acetate, bicarbonate, carbonate and the like. These agents advantageously present in amounts sufficient to maintain a pH of the system of between about 2 to about 9 and more preferably about 4 to about 8. As such the buffering agent may be as much as about 5% by weight of the total implant. Suitable water soluble preservatives include sodium bisulfite, sodium bisulfate, sodium thiosulfate, ascorbate, benzalkonium chloride, chlorobutanol, thimerosal, phenylmercuric acetate, phenylmercuric borate, phenylmercuric nitrate, parabens, methylparaben, polyvinyl alcohol, benzyl alcohol, phenylethanol and the like and mixtures thereof. These agents may be present in amounts of from about 0.001% to about 5% by weight and preferably about 0.01% to about 2% by weight. In at least one of the present implant, a benzylalkonium chloride preservative is provided in the implant, such as when the cyclic lipid therapeutic agent consists essentially of bimatoprost.

In some situations several implants can be implanted or inserted, each employing the same or different pharmacological agents. In this way, a cocktail of release profiles, giving a biphasic or triphasic release with a single administration is achieved, where the pattern of release may be greatly varied.

Additionally, release modulators such as those described in U.S. Pat. No. 5,869,079 may be included in the implant. The amount of release modulator employed will be dependent on the desired release profile, the activity of the modulator, and on the release profile of the cyclic lipid therapeutic agent in the absence of modulator. Electrolytes such as sodium chloride and potassium chloride may also be included in the implant. Where the buffering agent or enhancer is hydrophilic, it may also act as a release accelerator. Hydrophilic additives act to increase the release rates through faster dissolution of the material surrounding the drug in the implant, which increases the surface area of the drug exposed, thereby increasing the rate of drug bioerosion. Similarly, a hydrophobic buffering agent or enhancer dissolves more slowly, slowing the exposure of drug, and thereby slowing the rate of drug bioerosion.

In certain implants the combination of bimatoprost and a biodegradable polymer matrix is released or delivered an amount of bimatoprost between about 0.1 mg to about 0.5 mg for about 3-6 months after implantation into the eye. Various techniques can be employed to produce the implants described herein. Useful techniques include, but are not necessarily limited to, grinding methods, compression methods, extrusion methods, interfacial methods, molding methods, injection molding methods, combinations thereof and the like.

Compression methods can be used to make the implants, and typically yield implants with faster release rates than extrusion methods. Compression methods may use pressures of about 50-150 psi, more preferably about 70-80 psi, even more preferably about 76 psi, and use temperatures of about 0 degrees C. to about 115 degrees C., more preferably about 25 degrees C.

In one embodiment, a method for producing therapeutic polymeric implant comprises encapsulating a cyclic lipid therapeutic agent with a polymeric component to form a cyclic lipid-encapsulated implant. Such implant are effective in treating one or more ocular conditions, as described herein, and are suitable for administration to a patient into the subconjunctival space. The therapeutic activity of the cyclic lipid therapeutic agent remains stable during storage of the implant which may be attributed to the particular encapsulated form of the implant.

As discussed herein, the cyclic lipid therapeutic agent can comprises a single type of cyclic lipid derivative or derivatives. In certain embodiments, the cyclic lipid therapeutic agent comprises at least one prostamide derivative selected from the group consisting of bimatoprost, esters thereof, and mixtures thereof. In a further embodiment, the cyclic lipid therapeutic agent consists essentially of bimatoprost.

In additional embodiments, the cyclic lipid therapeutic agent can comprise combinations of two or more different cyclic lipid derivatives, such as a combination of bimatoprost and latanoprost, bimatoprost and travoprost, and the like.

The present methods are effective in producing encapsulated cyclic lipid therapeutic agent implant that maintain or preserve a substantial portion, if not all, of the therapeutic activity after a terminal sterilization procedure. It can be understood, that the present methods may also comprise a step of terminally sterilizing the implant. The implant can be sterilized before packaging or in their packaging. Sterilization of packages containing the present implant or implants is often preferred. The method may comprise exposing the present implant or implants to sterilizing amounts of gamma radiation, e-beam radiation, and other terminal sterilization products. In one embodiment, a method may comprise a step of exposing the present implant to gamma radiation at a dose of about 25 kGy.

As discussed herein, the polymeric component used in the present method can comprise a biodegradable polymer or biodegradable copolymer. In at least one embodiment, the polymeric component comprises a poly(lactide-co-glycolide) PLGA copolymer. In a further embodiment, the PLGA copolymer has a lactide/glycolide ratio of 75/25. In a still further embodiment, the PLGA copolymer has at least one of a molecular weight of about 63 kilodaltons and an inherent viscosity of about 0.6 dL/g. The present methods may also comprise a step of forming a first composition which comprises a cyclic lipid therapeutic agent, a polymeric component, and an organic solvent, and a step of forming a second oil-containing composition, and mixing the first composition and the second oil-containing composition.

The rate at which an implant degrades can vary, as discussed herein, and therefore, the present implant can release the cyclic lipid therapeutic agent for different periods of time depending on the particular configuration and materials of the implant. In at least one embodiment, an implant can release about 1% of the cyclic lipid therapeutic agent in the implant per day. In a further embodiment, the implant may have a release rate of about 0.7% per day when measured in vitro. Thus, over a period of about 40 days, about 30% of the cyclic lipid therapeutic agent may have been released.

As discussed herein, the amount of the cyclic lipid therapeutic agent present in the implant can vary. In certain embodiments, about 50% wt/wt of the implant is the cyclic lipid therapeutic agent. In further embodiments, the cyclic lipid therapeutic agent constitutes about 40% wt/wt of the implant.

The implant of the present invention can be inserted into the subconjunctival space of an eye by a variety of methods. The method of placement can influence the therapeutic component or drug-release kinetics. A preferred means of administration of the implant of the present invention is by subconjunctival injection. The location of the site of injection of the implant may influence the concentration gradients of therapeutic component or drug surrounding the element, and thus influence the delivery rate to a given tissue of the eye. For example, an injection into the conjunctiva toward the posterior of the eye will direct drug more efficiently to the tissues of the posterior segment, while a site of injection closer to the anterior of the eye (but avoiding the cornea) may direct drug more efficiently to the anterior segment.

The Implant can be administered to patients by administering an ophthalmically acceptable composition which comprises the implant to the patient. For example, implant may be provided in a liquid composition, a suspension, an emulsion, and the like, and administered by injection or implantation into the subconjunctival space of the eye.

The present implants or implant are configured to release an amount of cyclic lipid therapeutic agent effective to treat an ocular condition, such as by reducing at least one symptom of the ocular condition. More specifically, the implant may be used in a method to treat glaucoma, such as open angle glaucoma, ocular hypertension, chronic angle-closure glaucoma, with patent iridotomy, psuedoexfoliative glaucoma, and pigmentary glaucoma. By injecting the cyclic lipid therapeutic agent-containing implant into the subconjunctival space of an eye, it is believed that the cyclic lipid therapeutic agent is effective to enhance aqueous humor flow thereby reducing intraocular pressure. Additionally, subconjunctival delivery of implant containing a cyclic lipid therapeutic agent can to provide a therapeutic concentrations of the therapeutic agent to the retina of the eye.

The implants disclosed herein can be used to prevent or to treat various ocular diseases or conditions, including the following: maculopathies/retinal degeneration: macular degeneration, including age related macular degeneration (ARMD), such as non-exudative age related macular degeneration and exudative age related macular degeneration, choroidal neovascularization, retinopathy, including diabetic retinopathy, acute and chronic macular neuroretinopathy, central serous chorioretinopathy, and macular edema, including cystoid macular edema, and diabetic macular edema. Uveitis/retinitis/choroiditis: acute multifocal placoid pigment epitheliopathy, Behcet's disease, birdshot retinochoroidopathy, infectious (syphilis, lyme, tuberculosis, toxoplasmosis), uveitis, including intermediate uveitis (pars planitis) and anterior uveitis, multifocal choroiditis, multiple evanescent white dot syndrome (MEWDS), ocular sarcoidosis, posterior scleritis, serpignous choroiditis, subretinal fibrosis, uveitis syndrome, and Vogt-Koyanagi-Harada syndrome. Vascular diseases/exudative diseases: retinal arterial occlusive disease, central retinal vein occlusion, disseminated intravascular coagulopathy, branch retinal vein occlusion, hypertensive fundus changes, ocular ischemic syndrome, retinal arterial microaneurysms, Coat's disease, parafoveal telangiectasis, hemi-retinal vein occlusion, papillophlebitis, central retinal artery occlusion, branch retinal artery occlusion, carotid artery disease (CAD), frosted branch angitis, sickle cell retinopathy and other hemoglobinopathies, angioid streaks, familial exudative vitreoretinopathy, Eales disease. Traumatic/surgical: sympathetic ophthalmia, uveitic retinal disease, retinal detachment, trauma, laser, PDT, photocoagulation, hypoperfusion during surgery, radiation retinopathy, bone marrow transplant retinopathy. Proliferative disorders: proliferative vitreal retinopathy and epiretinal membranes, proliferative diabetic retinopathy. Infectious disorders: ocular histoplasmosis, ocular toxocariasis, presumed ocular histoplasmosis syndrome (POHS), endophthalmitis, toxoplasmosis, retinal diseases associated with HIV infection, choroidal disease associated with HIV infection, uveitic disease associated with HIV Infection, viral retinitis, acute retinal necrosis, progressive outer retinal necrosis, fungal retinal diseases, ocular syphilis, ocular tuberculosis, diffuse unilateral subacute neuroretinitis, and myiasis. Genetic disorders: retinitis pigmentosa, systemic disorders with associated retinal dystrophies, congenital stationary night blindness, cone dystrophies, Stargardt's disease and fundus flavimaculatus, Best's disease, pattern dystrophy of the retinal pigmented epithelium, X-linked retinoschisis, Sorsby's fundus dystrophy, benign concentric maculopathy, Bietti's crystalline dystrophy, pseudoxanthoma elasticum. Retinal tears/holes: retinal detachment, macular hole, giant retinal tear. Tumors: retinal disease associated with tumors, congenital hypertrophy of the RPE, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, intraocular lymphoid tumors. Miscellaneous: punctate inner choroidopathy, acute posterior multifocal placoid pigment epitheliopathy, myopic retinal degeneration, acute retinal pigment epithelitis and the like.

In at least one embodiment, a method of reducing intraocular pressure in an eye of a patient comprises administering an implant containing a cyclic lipid therapeutic agent, as disclosed herein, to a patient by subconjuctival injection. A syringe apparatus including an appropriately sized needle, for example, a 22 gauge needle, a 27 gauge needle or a 30 gauge needle, can be effectively used to inject the composition with into the subconjunctival space of an eye of a human or animal. Frequent repeat injections are often not necessary due to the extended release of the cyclic lipid therapeutic agent from the implant.

In certain implants, the implant preparation comprises a therapeutic component which consists essentially of bimatoprost, salts thereof, and mixtures thereof, and a biodegradable polymer matrix. The biodegradable polymer matrix can consist essentially of PLA, PLGA, or a combination thereof. When placed in the eye, the preparation releases about 40% to about 60% of the bimatoprost to provide a loading dose of the bimatoprost within about one day after subconjunctival administration. Subsequently, the implant release about 1% to about 2% of the bimatoprost per day to provide a sustained therapeutic effect. Such implant preparations may be effective in reducing and maintaining a reduced intraocular pressure, such as below about 15 mm Hg for several months, and potentially for one or two years.

Other implants disclosed herein can be configured such that the amount of the cyclic lipid therapeutic agent that is released from the implant within two days of subconjunctival injection is less than about 40% of the total amount of the cyclic lipid therapeutic agent in the implant. In certain formulations, 40% of the cyclic lipid therapeutic agent is not released until after about one week of injection. In certain implant formulations, less than about 30% of the cyclic lipid therapeutic agent is released within about one day of placement in the eye, and about 2% of the remainder is released for about 1 month after being placed in the eye. In another implant, less than about 20% of the cyclic lipid therapeutic agent is released within about one day of subconjunctival administration, and about 1% is released for about 2 months after such administration.

EXAMPLES

The following illustrative examples and are not intended to limit the scope of our invention.

Example 1

Method for Making Bimatoprost Microparticles

Biodegradable microparticles (microspheres) suitable for intraocular use were made by combining bimatoprost with a biodegradable polymer. Thus 800 mg of polylactic acid (PLA) was combined with 200 mg of bimatoprost. The combination was dissolved in 25 milliliters of dichloromethane. The mixture was then placed in a vacuum at 45° C. overnight to evaporate the dichloromethane. The resulting mixture was in the form of a cast sheet. The cast sheet was cut and ground in a high shear grinder with dry ice until the particles could pass through a sieve having a pore size of about 125 μm. The percent of bimatoprost present in the microparticles was analyzed using high pressure liquid chromatography (HPLC). The percent release of bimatoprost from the microparticles was profiled using dialysis. The percent of bimatoprost remaining in the recovered particles was analyzed by HPLC.

The release profile obtained is as shown in Table 1.

TABLE 1

| Time Point | Elapsed Time (Days) | Percent Released | Percent Per Day |
|---|---|---|---|
| Start | 0 | — | — |
| 1 | 1.03 | 47.51 | 47.51 |
| 2 | 2.03 | 47.92 | 0.41 |
| 3 | 3.03 | 49.99 | 2.07 |
| 4 | 4.03 | 50.09 | 0.10 |
| 5 | 7.04 | 50.90 | 0.82 |

The percent loading of bimatoprost was 14.93%. The percent of bimatoprost remaining in the recovered release particles was 4.94%.

Example 2

Extrusion and Compression Processes for Making Bimatoprost Implants

Bimatoprost is combined with a biodegradable polymer composition in a mortar. The combination is mixed with a shaker set at about 96 RPM for about 15 minutes. The powder blend is scraped off the wall of the mortar and is then remixed for an additional 15 minutes. The mixed powder blend is heated to a semi-molten state at specified temperature for a total of 30 minutes, forming a polymer/drug melt.

Rods are manufactured by pelletizing the polymer/drug melt using a 9 gauge polytetrafluoroethylene (PTFE) tubing, loading the pellet into the barrel and extruding the material at the specified core extrusion temperature into filaments. The filaments are then cut into about 1 mg size implants or drug delivery systems. The rods may have dimensions of about 2 mm long×0.72 mm diameter. The rod implants weigh between about 900 μg and 1100 μg.

Wafers are formed by flattening the polymer melt with a Carver press at a specified temperature and cutting the flattened material into wafers, each weighing about 1 mg. The wafers have a diameter of about 2.5 mm and a thickness of about 0.13 mm. The wafer implants weigh between about 900 μg and 1100 μg.

In-vitro release testing is performed by placing each implant into a 24-mL screw cap vial with 10 mL of Phosphate Buffered Saline solution at 37° C. 1 mL aliquots are removed and are replaced with equal volume of fresh medium on day 1, 4, 7, 14, 28, and every two weeks thereafter.

Drug assays are performed by HPLC, which consists of a Waters 2690 Separation Module (or 2695), and a Waters 996 Photodiode Array Detector. An Ultrasphere, C-18 (2), 5 μm; 4.6×150 mm column at 30° C. is used for separation and the detector is set at about 264 nm. The mobile phase is (10:90) MeOH—buffered mobile phase with a flow rate of 1 mL/min and a total run time of 12 min per sample. The buffered mobile phase may comprise (68:0.75:0.25:31) 13 mM 1-Heptane Sulfonic Acid, sodium salt—glacial acetic acid—triethylamine—Methanol. The release rates are determined by calculating the amount of drug being released in a given volume of medium over time in μg/day.

Polymers which may be used in the implants can be obtained from Boehringer Ingelheim. Examples of polymer include: RG502, RG502H, RG752, R202H, R203 and R206, and Purac PDLG (50/50). RG502 and RG502H are (50:50) poly(D,L-lactide-co-glycolide) with RG502 having an ester end group and RG502H having an acid end group, RG752 is (75:25) poly(D,L-lactide-co-glycolide), R202H is 100% poly (D, L-lactide) with acid end group or terminal acid groups, R203 and R206 are both 100% poly(D,L-lactide). Purac PDLG (50/50) is (50:50) poly(D,L-lactide-co-glycolide). The inherent viscosity of RG502, RG502H, RG752, R202H, R203, R206, and Purac PDLG are 0.2, 0.2, 0.2, 0.2, 0.3, 1.0, and 0.2 dL/g, respectively. The average molecular weight of RG502, RG502H, RG752, R202H, R203, R206, and Purac PDLG are, 11700, 11200, 11200, 6500, 14000, 63300, and 9700 daltons, respectively. The implants made can be suitable for intraocular use to treat an ocular condition.

Example 3

Bimatoprost/PLA/PLGA Intraocular Implants for Treating Glaucoma

A 72 year old female suffering from glaucoma in both eyes receives an intraocular implant containing bimatoprost and a combination of a PLA and PLGA in each eye. The implants weigh about 1 mg, and contain about 500 mg of bimatoprost. One implant is placed in the vitreous of each eye using a syringe. In about two days, the patient reports a substantial relief in ocular comfort. Examination reveals that the intraocular pressure has decreased: the average intraocular pressure measured at 8:00 AM has decreased from 28 mm Hg to 14.3 mm Hg. The patient is monitored monthly for about 6 months. Intraocular pressure levels remain below 15 mm Hg for six months, and the patient reports reduced ocular discomfort.

Example 4

Bimatoprost/PLA Intraocular Implants for Treating Ocular Hypertension

A 62 year old male presents with an intraocular pressure in his left eye of 33 mm Hg. An implant containing 400 mg of bimatoprost and 600 mg of PLA is inserted into the vitreous of the left eye using a trocar. The patient's intraocular pressure is monitored daily for one week, and then monthly thereafter. One day after implantation, the intraocular pressure is reduced to 18 mm Hg. By day 7 after implantation, the intraocular pressure is relatively stable at 14 mm Hg. The patient does not experience any further signs of elevated intraocular pressure for 2 years.

Example 5

Low Temperature Melt Extrusion Process for Making Bimatoprost Implants

The prostamide analog bimatoprost ((Z)-7-[1R,2R, 3R,5S)-3,5-Dihydoxy-2-[1E,3S)-3-hydroxy-5-phenyl-1-pentenyl]cyclopentyl]-5-N-ethylheptenamide) was incorporated into sustained release polymeric implants made by a low temperature (65° to 71° C.) melt extrusion process. The implants made comprised from 30 wt % to 50 wt % bimatoprost and from 50 wt % to 70 wt % poly(D,L-lactide-co-glycolide) polymer (a PLGA).

The implants were made at a temperature high enough to melt the bimatoprost and soften the polymer, yet low enough to avoid loss of substantial bimatoprost potency. The solubility parameters of the bimatoprost and the PLGA polymer used were similar so that the bimatoprost was soluble in the polymer thereby resulting in a solid solution at the temperature used. An extruded implant made from a solid solution of a therapeutic agent and a polymeric carrier can provide a more uniform and reproducible release profile of the therapeutic agent, as compared to an extruded implant where the bimatoprost is present as a solid dispersion in the polymeric carrier.

The polymer implants were made by melt extrusion in a piston driven extruder or Daca extruder/microcompounder. The implants are rod-shaped, but can be made in any geometric shape simply by changing the extrusion die.

The polymers were used as received from Boehringer Ingelheim and the bimatoprost was used as received from Torcan Chemical (Aurora, Ontario, Canada). To make an implant the polymer and bimatoprost were combined (see Table 2) in a Retsch ball-mill capsule with a ¼" stainless steel ball, and then the capsule was placed in the Retsch mill (Type MM200) for 5 min at 20-cycles/min. The capsule was then removed from the mill and the powder blend was stirred with a spatula. The capsule with the powder blend was mixed for 5 minutes on a Turbula mixer. The powder blend was inspected for homogeneity and the mixing procedure is repeated if necessary.

A steel powder funnel and a spatula were used to transfer the powder blend to an extruder barrel mounted in a pneumatic compaction press. A small amount of powder blend was added to the extruder barrel and the powder was compacted with the press set at 50 psi.

The powder-blend loaded barrel was placed in the extruder and allowed to equilibrate to a temperature of 65-71° C. The filaments were extruded at 0.0025"/sec through a 720-micron circular die to form the rod-shaped implant. The extruded filaments were smooth and had a consistent diameter. The Implant formulations made are shown in Table 2.

The filaments were cut into one-milligram rods (approximately 2 mm long) and their drug release over time monitored in phosphate buffered saline pH 7.4.

TABLE 2

| Bimatoprost Melt Extrusion Implant Formulations Implant Formulations | | |
|---|---|---|
| Bimatoprost wt % | Polymer 1 | Polymer 1 wt % |
| 30 | RG502 | 70 |
| 50 | RG502 | 50 |
| 30 | RG752 | 30 |
| 50 | RG752 | 50 |
| 30 | RG504 | 30 |
| 50 | RG504 | 50 |
| 30 | RG755 | 30 |
| 50 | RG755 | 50 |

A bimatoprost containing polymer implant can be used to deliver a controlled dose of bimatoprost to an ocular region to treat an ocular condition over an extended period of time.

A bimatoprost implant can also be made using a low-melting polymer such as a polycaprolactone. Additionally, instead of an extrusion method, direct compression of the polymer(s) with bimatoprost can be use to make a tablet implant suitable for intraocular use.

Example 6

Ultra Low Temperature Processes for Making Bimatoprost Implants

In this experiment we made additional bimatoprost containing polymeric sustained release implants suitable for intraocular administration. The implants were made by a melt extrusion process we developed for conduct at temperatures as low as about 57° C. Exemplary implants made contained 15% bimatoprost (the therapeutic agent), 10% polyethylene glycol (PEG 3350) (the co-solvent or second polymer), and 75% poly(D,L-lactide-co-glycolide) polymer (Resomer® RG752S, a PLGA) (the polymeric carrier or first polymer).

Typical extrusion temperatures for a PLGA implant are from about 85° C. to about 110° C. We determined that at an extrusion temperature of about 80° C. or higher, 50% or less of the bimatoprost is therapeutically inactive (loss of potency). See FIG. 1. As shown by FIG. 1, five different formulation bimatoprost containing sustained release implants or drug delivery systems ("DDS") were made. Proceeding from left to right to left along the x axis of FIG. 1 these five formulations were:

TABLE 3

Bimatoprost DDS (Implant) Formulations shown in FIG. 1

| | Formulation name | | | | |
| --- | --- | --- | --- | --- | --- |
| | 8092-096G | 8092-102G | 8092-097G | 8092-103G | 8092-108G |
| Bimatoprost wt % | 15 | 15 | 15 | 15 | 15 |
| Polymer type | RG504 | RG504 | RG504 | RG752S | RG752S |
| wt % | 75 | 70 | 65 | 70 | 75 |
| PEG 3350 wt % | 10 | 15 | 20 | 15 | 10 |

RG504 is a poly(D,L-lactide-co-glycolide (i.e. a PLGA) polymer resomer which is a 48:52 to 52:48 molar ratio (i.e. about 50:50) of D,L-lactide:glycolide. RG504 has an inherent viscosity of 0.45 to 0.60 dl/g in 0.1% chloroform at 25° C. (i.e. an average molecular weight of about 60,000) and is available from Boerhinger Ingelheim (Ridgefield, Conn.).

RG752S is also a poly(D,L-lactide-co-glycolide (i.e. a PLGA) polymer resomer, but comprises a 73:27 to 77:23 molar ratio (i.e. about 75:25) of D,L-lactide:glycolide. RG752S has an inherent viscosity of 0.16 to 0.24 dl/g, at a 0.1 wt % concentration in chloroform at 25° C. and is also available from Boerhinger Ingelheim (Ridgefield, Conn.).

The theoretical maximum potency of bimatoprost is by definition equal to the label strength ("LS") of the bimatoprost. For example, the label strength of a one milligram implant which comprises 150 ug of bimatoprost is 150 µg. Thus, if that implant is assayed and determined to release all 150 µg of the bimatoprost it contains over a certain time period, it can be said that the implant had a 100% potency. We determined the potency of the bimatoprost released from the implants made as a percent of their label strength using HPLC (high pressure liquid chromatography). Thus, the bimatoprost implants (each weighing about 1 mg) made were dissolved in 0.5 mL acetonitrile in a 10 mL volumetric flask and sonicated for 5 min. The flask was then filled to volume with diluent (72:18:10 water:acetonitrile:methanol); mixed well, and transferred to a HPLC vial for analysis.

The HPLC analysis was performed using a Waters Alliance 2695 HPLC system, Waters Symmetry®C18 reverse-phase column 4.6 mm×75 mm, and a Waters 2487 UV detector. The conditions for analysis were flow rate of 1.5 mL/minute, UV wavelength of 210 nm, column temperature of 30° C. and mobile phase of 72:18:10 (water:acetonitrile:methanol, v/v/v) with 0.03% (w/v) trifluoroacetic acid. The injection volume of samples and standards assayed was 75 uL with a cycle time of 45 min.

As shown by FIG. 1, the potency of the bimatoprost released from the DDS made increased from about 40% when the DDS was made by a melt extrusion process carried out at 85° C., to more than about 90% potency when the DDS was made by a melt extrusion process carried out at 57° C. Thus, the potency of the bimatoprost was inversely proportional to the temperature at which the melt extrusion process used to make the DDS was carried out. The use of different resomers and presence of PEG 3350 in the DDS formulations has no relevance to this finding of higher temperature being correlated to lower bimatoprost potency. In other words, the use of a different resomer, the use of a different resomer in a different amount and the inclusion of a PEG 3350 in the DDS formulation did not affect the temperature to which the bimatoprost was exposed.

Thus, knowing that bimatoprost is a heat sensitive therapeutic agent we developed a very low temperature melt extrusion process for making bimatoprost containing implants. To make a DDS by a melt extrusion process wherein at least about 50% of the bimatoprost is biologically active (i.e. has a potency at least 50% of the LS) requires reducing the extrusion temperature to less than about 80° C. Since the melting point of most resomers, including PLGAs, used to make a DDS exceeds about 80° C. it is not sufficient merely to lower the extrusion temperature, as to do so would merely provide a partially or poorly melted polymer in which the active agent is far from homogenously distributed. A non-homogenous distribution of the active agent in the polymer of the DDS can result in a burst release effect followed thereafter by wide oscillations in the amount and rate of release of the active agent from the polymer. Such a deficient DDS would have no therapeutic utility.

The goal therefore was to make an extruded PLGA-bimatoprost implant by a process that reduces the extrusion temperature and yet maintains a homogenous mixture of (preferably non-crystalline) bimatoprost within the polymeric matrix of the DDS (implant).

We determined based on an analysis of solubility parameters, that bimatoprost is soluble in the PLGA polymers (the polymer carriers or first polymers) used. Hence a solid solution of the bimatoprost and the polymers used can be formed as the polymers are heated. Forming a solid solution of a bimatoprost and a PLGA at a low temperature can avoid the occurrence of substantial loss of bimatoprost potency. Additionally, forming a solid solution of the bimatoprost and a similar solubility parameter PLGA (through use of a suitable co-solvent) has the additional advantage that the bimatoprost is prevented from re-crystallizing in the final extruded implant, since the implant is a solid solution of the bimatoprost and the PLGA in the co-solvent. Hence, no bimatoprost polymorphs are present in the implant. Finally, the bimatoprost is homogenously distributed throughout the polymer, as compared to the distribution of the bimatoprost in the solid dispersion that is made when the bimatoprost and a PLGA are mixed together, the polymer melted and the melted mixture extruded to make a DDS. In a solid dispersion implant the bimatoprost is present in the form of crystals or particles of the bimatoprost.

As noted, the PLGA polymers are not sufficiently molten at the lower extrusion temperatures needed to retain the potency of bimatoprost above about 50% of LS. We discovered that by addition of a low-melting polymeric cosolvent (such as a PEG) with the same (or substantially the same) solubility parameter as the bimatoprost and the polymer used permitted the extrusion temperature to be lowered to as low as 57° C. The potency of the bimatoprost was thereby preserved. Additionally, we found that the PEG containing DDS formulations we developed has a reduced "burst" release normally associated with drugs as water soluble as bimatoprost. FIGS. 2 and 3 show respectively the total percent bimatoprost release and the daily microgram of bimatoprost released from an exemplary DDS formulation we made: in both FIGS. 2 and 3 the formulation observed was the Table 3 8092-108G formulation.

FIG. 2 shows the total amount of bimatoprost released from the 8092-108G DDS over a fifty day period. From about day 8 to about day 40 (a 32 day period) the release rate was linear. FIG. 3 shows the daily amount of bimatoprost released from the 8092-108G DDS over a fifty day period. From about day 13 to about day 42 (a 29 day period) the daily release rate was between about 3.3 μg of bimatoprost per day and 2.5 μg of bimatoprost per day, meaning that during that 29 period the daily rate of release did not vary by more than about 32%. From about day 13 to about day 38 (a 25 day period) the daily release rate was between about 3.3 μg of bimatoprost per day and 3.0 μg of bimatoprost per day, meaning that during that 25 day period the daily rate of release did not vary by more than about 10%.

Our selection of a PEG as a cosolvent for the bimatoprost and the PLGA was based upon our analysis and comparison the solubility parameters of the three components (PEG, bimatoprost and PLGAS) of the DDS. Thus the solubility parameters set forth in Table 4 show that bimatoprost can be predicted to be soluble in both PLGA polymer and in PEG 3350. Furthermore, comparison the respective solubility parameters shows that the PEG 3350 can be predicted to be soluble in the PLGA. Hence it can be predicted that upon melting the PEG 3350 at it's low melt temperature, the PEG 3350 can effectively plasticizing the PLGA and allow it to be extruded at the lower PEG 3350 melt temperature. This same principle can be applied generally to other low-melting polymers such as polycaprolactones as long as their solubility parameter does not differ from the drug and PLGA by more than 10 $(MPa)^{1/2}$. Other polymers can be used to provide different blending and release characteristics. Our preferred formulation method is melt extrusion, but a suitable implant can also be made by direct compression or solvent casting of the polymer(s) with bimatoprost. The implants we made in this experiment were cylindrically shaped but suitable implant can also be made with other cross-sectional shapes by changing the extrusion die.

The polymer implants we made in this experiment were made by melt extrusion at temperatures as low as 57° C. using a Daca extruder/microcompounder (Daca Instruments, Inc., Goleta, Calif.). The PLGA resomers (polymers) were used as received from Boehringer Ingelheim. PEG 3350 and the bimatoprost were used as received from Sigma Aldrich, and Torcan Chemical, respectively. The polymers (PLGA and PEG 3350) and bimatoprost were combined in a stainless steel container with two ¼" stainless steel balls and mixed on a Turbula mixer for 15 minutes. The container was removed and the content is stirred with a spatula. It was then returned to Turbula mixer for an additional 15 minutes, after which the powder blend was inspected for homogeneity and the mixing procedure repeated if necessary.

The powder-blend was fed into the extruder at a controlled rate. The filament DDS was extruded through a 720 micron diameter circular die forming cylindrically-shaped implant. The extruded filaments had a smooth surface with a consistent diameter. The filaments are cut into one-milligram rods (approximately 2 mm long) and then placed into phosphate buffered saline pH 7.4 (0.01 M) where their drug release in monitored in vivo over time by HPLC.

TABLE 4

Solubility Parameters for DDS Components

| Component | Solubility Parameter, $MPa^{1/2}$ |
|---|---|
| Bimatoprost (192024) | 17-19 |
| Resomer ® RG752s | 21 |
| Polyethylene Glycol 3350 | $20^c$ |

In Table 4 MPa is an abbreviation for milli-Pascals.

All references, articles, publications and patents and patent applications cited herein are incorporated by reference in their entireties. While this invention has been described with respect to various specific examples and embodiments, our invention is not limited thereto and that it can be variously practiced within the scope of the following claims.

We claim:

1. A low temperature process for making an intraocular implant, the process comprising the steps of:
   (a) combining a cyclic lipid therapeutic agent, a polymer, and a low melting cosolvent to form a mixture;
      wherein the solubility parameters of the cyclic lipid therapeutic agent, the polymer, and the low melting cosolvent are all within about 10 $Mpa^{1/2}$ of each other;
      wherein the low melting cosolvent has a melt temperature of between about 50° C. and about 80° C.;
      wherein the cyclic lipid therapeutic agent is selected from the group consisting of bimatoprost, latanoprost, travoprost, unoprostone, prostaglandin E1, prostaglandin E2, and mixtures thereof;
      wherein the polymer is a biodegradable polymer selected from the group consisting of polylactic acid, polyglycolic acid, and polylactide-co-glycolide; and
      wherein the low melting cosolvent is selected from the group consisting of decafluorobutane, poly(hexamethylene adipamide), and polyethylene glycol 3350;
   (b) heating the mixture to a temperature between about 50° C. and about 80° C., and;
   (c) extruding the heated mixture, thereby making an implant suitable for intraocular use, wherein the cyclic lipid therapeutic agent comprises 20% by weight of the intraocular implant, and wherein the potency of the cyclic lipid therapeutic agent released from the implant is at least about 50% of its maximum potency.

2. The process of claim 1 wherein the cyclic lipid therapeutic agent is bimatoprost.

3. The process of claim 2, wherein the low melting cosolvent is polyethylene glycol 3350, wherein the polymer is a polylactide-co-glycolide, wherein the cyclic lipid therapeutic agent is bimatoprost, and wherein the mixture is extruded at a temperature of 65° C.

4. The process of claim 1, wherein the low melting cosolvent is decafluorobutane.

5. The process of claim 1, wherein the low melting cosolvent is poly(hexamethylene adipamide).

* * * * *

UNITED STATES PATENT AND TRADEMARK OFFICE
CERTIFICATE OF CORRECTION

PATENT NO.         : 8,846,073 B2
APPLICATION NO.    : 11/612928
DATED              : September 30, 2014
INVENTOR(S)        : Lon T. Spada et al.

It is certified that error appears in the above-identified patent and that said Letters Patent is hereby corrected as shown below:

In the Specification

In column 3, line 35, delete "application" and insert -- applications --, therefor.

In column 6, line 6, after "is" delete "are".

In column 7, line 64, delete "or and" and insert -- and/or --, therefor.

In column 9, line 43, after "the" delete "a".

In column 9, line 51, after "the" delete "a".

In column 9, line 59, after "the" delete "a".

In column 21, line 22, delete "canula" and insert -- cannula --, therefor.

In column 22, line 18, delete "loradatine," and insert -- loratadine, --, therefor.

In column 22, line 22-23, delete "trimprazine" and insert -- trimeprazine --, therefor.

In column 22, line 23, delete "chiorcyclizine," and insert -- chlorcyclizine, --, therefor.

In column 22, line 27, delete "cefutoxime," and insert -- cefuroxime, --, therefor.

In column 22, line 43, delete "flurometholone," and insert -- fluorometholone, --, therefor.

In column 22, line 46, delete "riamcinolone hexacatonide," and
insert -- triamcinolone hexacetonide, --, therefor.

In column 22, line 50, delete "duanorubicin," and insert -- daunorubicin, --, therefor.

In column 22, line 62, delete "valciclovir," and insert -- valaciclovir, --, therefor.

In column 22, line 67, delete "astazanthin," and insert -- astaxanthin, --, therefor.

In column 23, line 2, delete "quercitin," and insert -- quercetin, --, therefor.

In column 23, line 29, delete "anyhdrase" and insert -- anhydrase --, therefor.

In column 26, line 9, delete "serpignous" and insert -- serpiginous --, therefor.

In column 26, line 18, delete "angitis," and insert -- angiitis, --, therefor.

In column 26, line 56, delete "subconjuctival" and insert -- subconjunctival --, therefor.

Signed and Sealed this
Thirtieth Day of December, 2014

Michelle K. Lee
*Deputy Director of the United States Patent and Trademark Office*